United States Patent
Takahashi

(10) Patent No.: US 6,747,736 B2
(45) Date of Patent: Jun. 8, 2004

(54) TERAHERTZ WAVE SPECTROMETER

(75) Inventor: Hironori Takahashi, Hamamatsu (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 315 days.

(21) Appl. No.: 10/020,982

(22) Filed: Dec. 19, 2001

(65) Prior Publication Data

US 2002/0067480 A1 Jun. 6, 2002

Related U.S. Application Data

(63) Continuation-in-part of application No. PCT/JP00/04048, filed on Jun. 21, 2000.

(30) Foreign Application Priority Data

Jun. 21, 1999 (JP) ............................................ 11-174214

(51) Int. Cl.[7] ................. G01J 3/42; G01J 3/30
(52) U.S. Cl. ........................ 356/319; 356/326
(58) Field of Search ................. 356/317, 318, 356/319, 320, 326; 250/338.1

(56) References Cited

U.S. PATENT DOCUMENTS

| | | | |
|---|---|---|---|
| 5,623,145 A | 4/1997 | Nuss | |
| 5,710,430 A | 1/1998 | Nuss | |
| 5,939,721 A | 8/1999 | Jacobsen et al. | |
| 6,078,047 A | * 6/2000 | Mittleman et al. | 250/338.1 |
| 6,479,822 B1 | * 11/2002 | Nelson et al. | 250/341.1 |

FOREIGN PATENT DOCUMENTS

| | | |
|---|---|---|
| JP | A 7-209352 | 8/1995 |
| JP | A 8-320254 | 12/1996 |
| JP | A 10-153547 | 6/1998 |
| JP | 2003083888 A | * 3/2003 |
| WO | WO 97/45747 | 12/1997 |

OTHER PUBLICATIONS

Eric Mueller, Terahetz Radiation: Applications and Sources, The Industrial Physicist, pp.27–29.*
Sakai et al., "Terahertz Electromagnetic Waves: Generation and Applications", *Laser Review*, vol. 26, No. 7, pp. 515–521(1998).

(List continued on next page.)

*Primary Examiner*—Frank G. Font
*Assistant Examiner*—Layla Lauchman
(74) *Attorney, Agent, or Firm*—Oliff & Berridge, PLC

(57) ABSTRACT

A terahertz wave detector is for detecting a terahertz wave which is emitted from a terahertz wave generator and which is transmitted through a sample. The timing, at which a probe light is irradiated on an optical switching device in the terahertz wave detector, is vibratingly varied by driving a movable reflector in a variable optical delay device at a predetermined vibration frequency. The resultant detection signal generated thereby and changing periodically and vibratingly is subjected to frequency analysis by a spectrum analyzer in a spectroscopic processor. The detection signal has the same temporal waveform as that of the terahertz wave and subjected to scale conversion. Therefore, the frequency analysis of the detection signal enables frequency measurement of a terahertz wave in real time. As a result, real-time spectroscopy is possible, and the device configuration is simplified.

19 Claims, 25 Drawing Sheets

OTHER PUBLICATIONS

Hu et al., "Imaging with terahertz waves", Optics Letters, vol. 20, No. 16, Aug. 15, 1995, pp. 1716–1719.

Wu et al., "Free–space electro–optics sampling of mid–infrared pulses", Appl. Phys. Lett., vol. 71, No. 10, Sep. 8, 1997, pp. 1285–1286.

Zhang et al., "Electro–Optic Imaging of THz Beams", Springer Series in Chemical Physics, vol. 62, 1996, pp. 54–55.

Copies from "Practical Handbook (2) of Electronic Circuits", (1975), CQ Publications Kabushiki Kaisha, (w/abstract).

Yasa et al., "A Rapid–Scanning Autocorrelation Scheme for Continuous Monitoring of Picosecond Laser Pulses", Optics Communications, vol. 36, No. 5, 1981, pp. 406–408.

Tearney et al., "High–speed phase– and group–delay scanning with a grating–based phase control delay line", Optics Letters, vol. 22, No. 23, 1997, pp. 1811–1813.

Copies from "Spectrum Analysis Basics" (1998), Hewlett–Packard, pp. 3–5, 3–6, 3–7, 3–16.

Mittleman, et al., "T–Ray Imaging", IEEE Journal of Selected Topics in Quantum Electronics, vol. 2, No. 3, Sep. 1996, pp. 679–692.

Cai et al., "Coherent terahertz radiation detection: Direct comparison between free–space electro–optic sampling and antenna detection", Applied Physics Letters, vol. 23. No.4, Jul. 27, 1998, pp. 444–446.

* cited by examiner

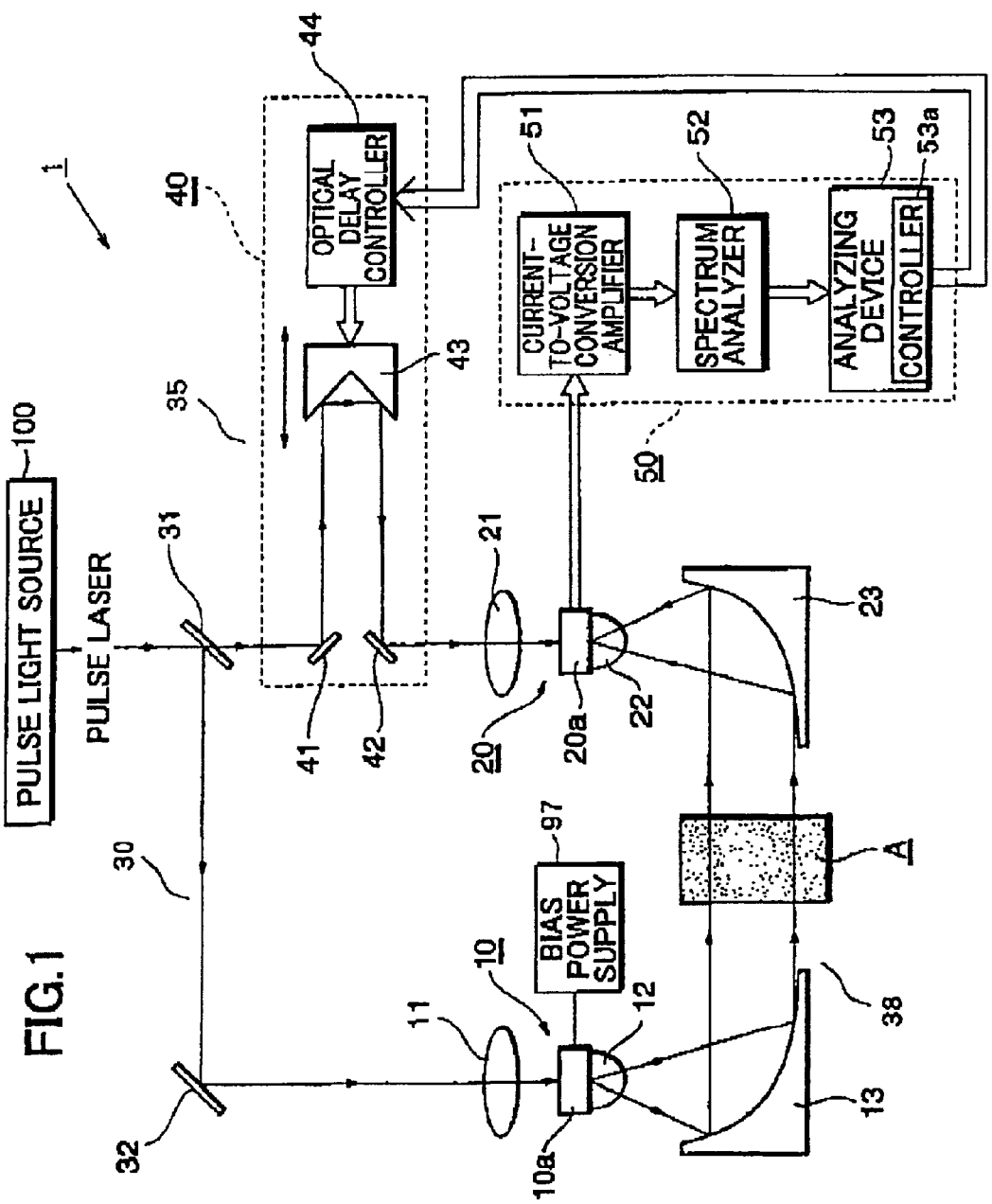

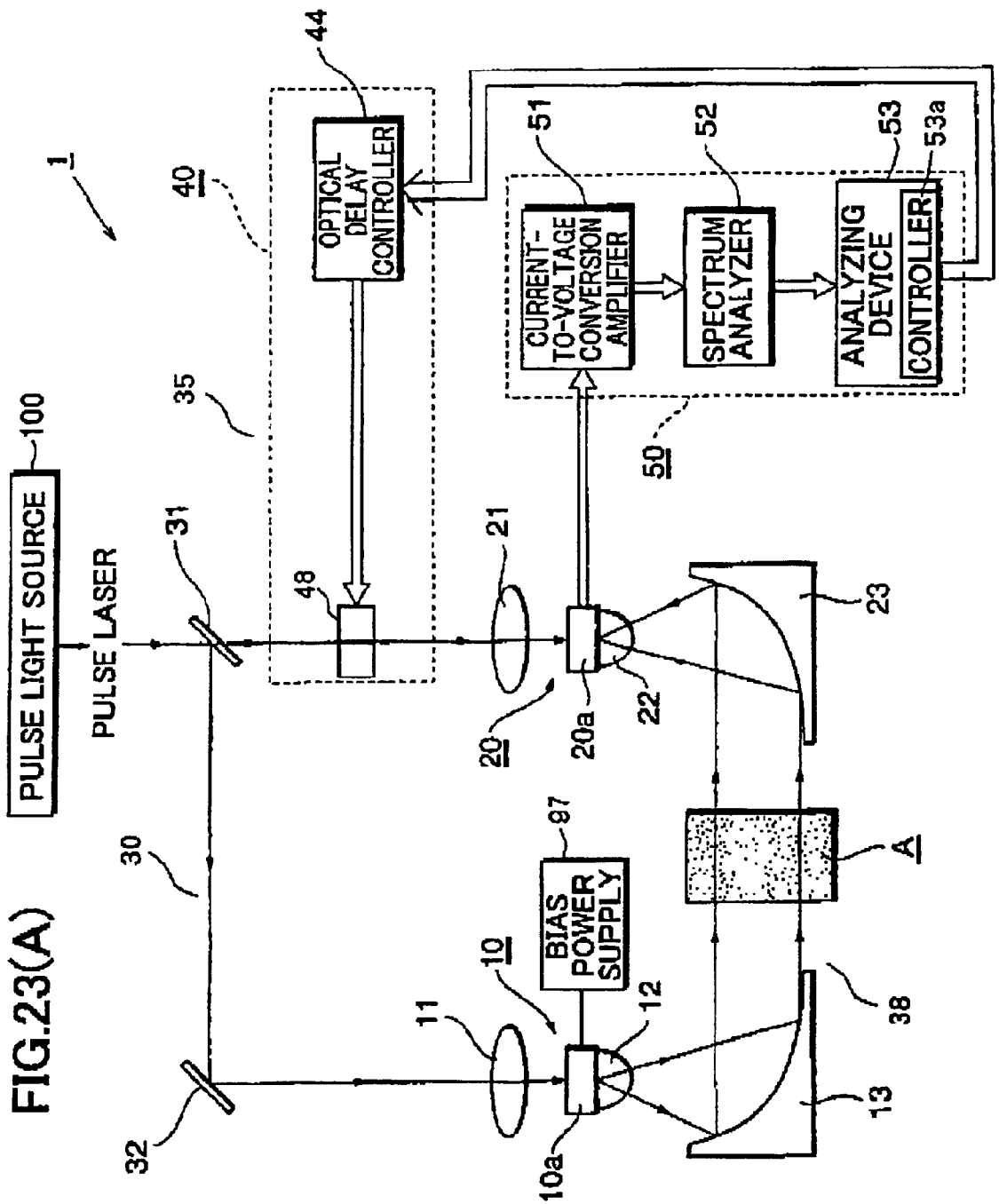

TERAHERTZ WAVE SPECTROMETER

CROSS-REFERENCE TO RELATED APPLICATION

This application is a continuation-in-part of International Application No. PCT/JP00/04048 filed on Jun. 21, 2000 by Hironori Takahashi, which was not published in the English language and which claims the benefit of Japanese Patent Application No. 11-174214, filed Jun. 21, 1999.

BACKGROUND OF THE INVENTION

1. Field of the Invention

The present invention relates to a terahertz wave spectrometer for performing spectroscopic measurements by using a terahertz wave. The terahertz wave is an electromagnetic wave having a frequency of around 1 THz (terahertz).

2. Description of Related Art

An electromagnetic-wave frequency range of around 1 THz (terahertz) is located on the boundary between an optical wave and a radio wave, and is called a terahertz range. More specifically, the terahertz range is defined as a frequency range that includes frequencies of about 100 GHz to 10 THz. The terahertz range can sometimes be defined as a wider frequency range that includes the range of about 100 GHz to 10 THz and further includes neighboring lower- and higher-frequency ranges. For example, the terahertz wave can effectively be used in spectroscopic processes for an infrared region and in imaging processes for the infrared region.

In comparison with other frequency ranges, developments of generators and detectors for this frequency range advance relatively slowly. Many technological and other problems have not yet been solved to apply the generators and detectors in practical uses. It is necessary to develop terahertz wave generators (optical sources) and terahertz wave detectors so that they will be small and easy to handle, in order to realize, in an industrial field, a spectrometer that detects and quantitatively measures the characteristics of a sample by using terahertz wave.

There are recently being developed terahertz wave generators (optical sources) and terahertz wave detectors that employ optical switching devices or electro-optic (EO) crystals. Though it is difficult to generate electromagnetic wave at the terahertz-range frequency by using an electric-circuit oscillator, it is possible to generate and detect electromagnetic wave at the terahertz-range frequency by modulating an electric current, or the like, using a pulse-shaped light.

In order to attain the spectroscopic measurement by using terahertz wave, one method has been proposed to detect terahertz wave and to measure directly the intensity of the temporal waveform of the detected terahertz wave. However, this method provides no limitation or no selection onto the respective frequency components of the terahertz wave. Accordingly, even if the sample presents some special characteristic with respect to a specific frequency range, it is impossible to perform measurement at the specific frequency range only. Thus, only a limited amount of information can be obtained from the spectroscopic process.

A method for performing measurements with frequency selection has been proposed by "Terahertz Electromagnetic Wave: Generation and Applications" by Sakai et al. *Laser Review*, Vol. 26, No.7, pp.515–521 (1998). During the measurement process with frequency selection, a detector performs a sampling measurement. A temporal waveform of the terahertz wave is determined based on the sampling-measurement result. Next, the obtained temporal waveform is subjected to fast Fourier transform (FFT), and the resultant amplitude spectrum is evaluated. In this device, the terahertz wave is scanned only once in a forward direction by a variable optical delay device, thereby sampling the terahertz wave.

Japanese Patent Unexamined Application Publication Nos. 8-320254 and 10-153547 disclose imaging systems that obtain spectroscopic information by using terahertz wave and by using an analog-to-digital converter and a digital signal processor (DSP). According to the methods disclosed by these publications, the DSP retrieves frequency-related information from time domain data by recognizing the characteristic shape of the terahertz wave.

According to the above-described conventional methods, the temporal waveform is first measured, and then frequency-related information, such as an amplitude spectrum, is determined by a computer thereafter. It is therefore impossible to attain a real-time measurement. Additionally, the entire device for attaining those methods has a complicated structure. Especially, the analog-to-digital converter and the DSP are employed to attain the methods disclosed by the publication Nos. 8-320254 and 10-153547. Accordingly, the device, such as a two-dimensional array for performing an imaging operation, becomes complicated and expensive,

SUMMARY OF THE INVENTION

It is an objective of the present invention to solve the above-described problems, and to provide a terahertz wave spectrometer, which can perform spectroscopic measurement in real time and whose device structure is simplified.

In order to overcome the above-described problem, the present invention provides a terahertz wave spectrometer for performing spectroscopic measurement by using terahertz wave, comprising: a predetermined excitation light optical system guiding an excitation light; a terahertz wave generator generating terahertz wave by using the excitation light guided by the predetermined excitation light optical system; a terahertz wave optical system guiding the terahertz wave generated by the terahertz wave generator to a sample for spectroscopic measurement, and further guiding the terahertz wave which has been affected by the sample; a predetermined probe light optical system guiding a probe light that is in synchronization with the excitation light; a terahertz wave detector detecting, using the probe light guided by the predetermined probe light optical system, the terahertz wave that is affected by the sample and that is guided by the terahertz wave optical system, and outputting a detection signal; optical delay vibrating means provided in either one of the excitation light optical system and the probe light optical system, the optical delay vibrating means vibrating, at a predetermined vibration frequency, the length of the optical path of the corresponding one of the excitation light and the probe light, thereby periodically vibrating the irradiation timing of the corresponding one of the excitation light and the probe light onto a corresponding one of the terahertz wave generator and the terahertz wave detector; and spectroscopic processing means performing spectroscopic measurement on the sample based on the detection signal obtained by the terahertz wave detector, the spectroscopic processing means including frequency analyzing means performing frequency analysis on the detection signal that periodically changes in accordance with the vibration frequency, the frequency analyzing means performing the frequency analysis of the detection signal by performing a frequency domain measurement, the frequency-analysis result obtained by the frequency analyzing means indicating frequency-analysis information on the terahertz wave that has been affected by the sample, thereby indicating the spectroscopic information of the sample.

In the terahertz wave spectrometer having the above-described structure, the irradiation timing of the probe light onto the terahertz wave detector is synchronized with respect to the irradiation timing of the excitation light onto the terahertz wave generator, while vibrating or oscillating the difference between the probe light irradiation timing and the excitation light irradiation timing. More specifically, the terahertz wave spectrometer is set up so that the terahertz wave emitted from the terahertz wave generator is transmitted through the predetermined terahertz wave optical system, is affected by the sample upon passing through or reflecting off the sample, for example, and then falls incident on the terahertz wave detector, which in turn detects the terahertz wave by using the probe light. The terahertz wave spectrometer is set up to vibrate or oscillate the irradiation timing of the terahertz wave on the terahertz wave detector and the detection timing of the terahertz wave by the probe light at the terahertz wave detector.

In the case where the optical delay vibrating means is provided in the probe light optical system, the optical delay vibrating means preferably includes a portion constructed to change the length of the optical path of the probe light. By driving this portion at a predetermined frequency, the detection timing of the terahertz wave periodically vibrates or oscillates. It is noted that by changing the detection timing, it is possible to scan the temporal waveform of the terahertz wave. According to the present invention, because the detection timing is changed in a vibrating or oscillating manner, the temporal waveform of the detection signal has a time scale converted from the time scale of the temporal waveform of the terahertz wave. The temporal waveform of the detection signal has a shape converted from the shape of the temporal waveform of the terahertz wave in a predetermined rule. For example, the shape of the temporal waveform of the detection signal may be exactly the same as the shape of the temporal waveform of the terahertz wave. Or, the shape of the temporal waveform of the detection signal may be the quasi-same, or similar, with the shape of the temporal waveform of the terahertz wave. Or, the shape of the temporal waveform of the detection signal may correspond to the shape of the temporal waveform of the terahertz wave by a predetermined rule. The frequency spectrum of the detection signal has a frequency scale converted from the frequency scale of the frequency spectrum of the terahertz wave. The frequency spectrum of the detection signal has a shape converted from the shape of the frequency spectrum of the terahertz wave in a predetermined rule. For example, the shape of the frequency spectrum of the detection signal may be exactly the same as the shape of the frequency spectrum of the terahertz wave. Or, the shape of the frequency spectrum of the detection signal may be the quasi-same, or similar, with the shape of the frequency spectrum of the terahertz wave. Or, the shape of the frequency spectrum of the detection signal may correspond to the shape of the frequency spectrum of the terahertz wave by a predetermined rule. By vibrating or oscillating the detection timing, it is therefore possible to convert the frequency scale of the terahertz (THz) order into a desired frequency scale, such as a kilohertz (kHz) order, for example.

Alternatively, the optical delay vibrating means may be provided to the excitation light optical system, rather than to the probe light optical system, thereby vibrating the terahertz wave generating timings. Also in this case, it is possible to attain scale conversion onto the temporal waveform and onto the frequency spectrum.

According to the present invention, by performing frequency domain measurement onto the detection signal by the frequency analyzing means, it is possible to measure the frequency of the detection signal directly. The thus obtained frequency information of the detection signal is frequency-scale converted frequency information of the terahertz wave, and therefore indicates the spectroscopic information of the sample. By measuring the frequency of the detection signal directly in this way, it is possible to perform spectroscopic measurement of the sample.

In this way, according to the present invention, the frequency of the detection signal is measured directly. Accordingly, contrary to the conventional technology that performs time domain measurement, it becomes unnecessary to perform fast Fourier Transform calculation or the like. It therefore becomes possible to perform real-time measurement. Because it is unnecessary to perform the fast Fourier Transform calculation or the like, it is possible to perform frequency analysis on the terahertz wave by using the simplified data processing method and by using the simplified device configuration. Accordingly, it is possible to realize a spectrometer which can attain a real-time spectroscopic measurement, whose device structure is simplified, and which can be made less costly. Simplifying the structure allows the device to be assembled into an integrated circuit configuration.

The optical path length (and therefore the detection timing) may be vibrated or oscillated in a triangular waveform or a sawtooth waveform, in order to linearly scale-convert the temporal waveform and the frequency spectrum of the terahertz waveform into those of the detection signal while exactly maintaining the shapes of the temporal waveform and the frequency spectrum. The optical path length (and therefore the detection timing) may be vibrated or oscillated in a sinusoidal waveform, in order to nonlinearly scale-convert the temporal waveform and the frequency spectrum of the terahertz waveform into those of the detection signal while converting the shapes of the temporal waveform and the frequency spectrum into the quasi-same shapes. The vibration waveform may be optionally selected so that the detection signal will correspond to the original terahertz wave with a conversion rule that is proper for the device configuration and for the measuring conditions.

The frequency analyzing means may preferably include a spectrum analyzer producing a frequency spectrum by performing a frequency analysis on the detection signal. In this case, the produced frequency spectrum is indicative of the spectroscopic information of the sample. Measurements can be attained under various conditions. For example, measurements can be attained by narrowing the measurement frequency range of the spectrum analyzer, or by limiting the measurement frequency range to a specific frequency.

The frequency analyzing means may include a band pass filter selecting a predetermined frequency component from the detection signal. In this case, the detection signal at the selected frequency component is indicative of the spectroscopic information of the sample. The device structure can be further simplified by thus using the band-pass filter.

The band pass filter may include a plurality of band pass filters for selecting frequency components different from one another, and the spectroscopic processing means may further include correlation analyzing means determining a correlation between the plurality of frequency components selected by the plurality of band pass filters. By using the correlation, such as a difference, between the plural frequency components, it is possible to obtain a greater amount of spectroscopic information, and also to enhance the efficiency in the spectroscopic measurement.

The spectroscopic processing means may further include frequency setting/changing means controlling the optical delay vibrating means and changing or setting the value of the vibration frequency, at which the optical delay vibrating means vibrates the length of the optical path for the corresponding one of the excitation light and the probe light, the frequency analyzing means performing the frequency analysis based on the thus changed or set vibration frequency. It is possible to freely control the condition of the time/frequency scale conversion from the terahertz wave into the detection signal, thereby freely changing and setting the frequency range to be detected.

In order to construct the terahertz wave generator or the terahertz wave detector as suitable for generation or detection of the terahertz wave, for example, at least one of the terahertz wave generator and the terahertz wave detector may be constructed from an optical switching device. Alternatively, at least one of the terahertz wave generator and the terahertz wave detector may be constructed from an electro-optic crystal.

The terahertz wave spectrometer may further comprise sample moving means moving the sample two-dimensionally, thereby causing the spectroscopic processing means to perform two-dimensional spectroscopic measurement on the sample.

Alternatively, the terahertz wave detector may preferably be constructed from a two-dimensional detector for performing a two-dimensional spectroscopic measurement on the sample under investigation. That is, the terahertz wave detector may be constructed from a two-dimensional detector, in which a plurality of terahertz wave detecting portions are arranged two-dimensionally, the spectroscopic processing means including a plurality of frequency analyzing means, the plural terahertz wave detecting portions being connected to the plural frequency analyzing means, respectively, each frequency analyzing means performing frequency analysis on a detection signal obtained by the corresponding terahertz wave detecting portion, thereby attaining two-dimensional spectroscopic measurement on the sample. With this structure, it is possible to attain measurement, such as a two-dimensional imaging, on the sample in real time. This is effective to the spectroscopic measurement to measure distribution of components in the sample.

The excitation light optical system may include an optical chopper controlling on and off of the excitation light. In this case, it is possible to enhance the signal-to-noise ratio of the measurement by reducing the influences from the 1/f noise, which is generated by the source for the excitation light and the probe light.

The spectroscopic processing means may further include analyzing means determining frequency analysis of the terahertz wave, which is affected by the sample and which indicates the spectroscopic information of the sample, based on the frequency-analysis result of the detection signal obtained by the frequency analyzing means. The analyzing means performs processings, such as converting the frequency scale of the frequency-analysis result of the detection signal back to the frequency scale of the original terahertz wave, thereby obtaining frequency-analysis information of the terahertz wave, that is, the spectroscopic information of the sample.

In this way, in the terahertz wave spectrometer of the present invention, the optical delay vibrating means vibrates the irradiation timings of the probe light or the excitation light at the predetermined frequency, thereby causing the detection signal obtained by the terahertz wave detector to have a signal waveform whose time scale is converted from the time scale of the temporal waveform of the terahertz wave. Additionally, the frequency analyzing means, which employs the spectrum analyzer, the band-pass filter, or the like, is applied to the detection signal which has such a signal waveform. Frequency analysis is performed on the detection signal whose frequency scale is converted from the frequency scale of the terahertz wave. Spectroscopic measurement is attained based on the analyzed result output. Accordingly, it is possible to realize a terahertz wave spectrometer which can perform real-time spectroscopic measurement of terahertz wave, including the two-dimensional imaging, whose device structure is simplified, which can be made less costly, and which can be assembled into an integrated circuit structure. It is also possible to enhance the signal-to-noise ratio of the spectroscopic measurement. It is therefore possible to attain a more accurate measurement, and to reduce the period of time required to attain the measurement. The terahertz wave spectrometer of the present invention can enable the terahertz wave spectroscopy to be applied to a wider area of practical use.

The frequency analyzing means may preferably detect a desired frequency component of the detection signal by performing the frequency-domain measurement. The frequency analyzing means may be constructed from a spectrum analyzer. The spectrum analyzer may be set to a zero span mode. Or, the frequency analyzing means may include a band pass filter selecting the desired frequency component, and the spectroscopic processing means may further include frequency setting/changing means controlling the optical delay vibrating means and changing or setting the value of the vibrating frequency, at which the optical delay vibrating means vibrates the length of the optical path of the corresponding one of the excitation light and the probe light, to a value that corresponds to a frequency value of the desired frequency component to be selected by the band pass filter. The terahertz wave detector may be constructed from a two-dimensional detector, in which a plurality of terahertz wave detecting portions are arranged two-dimensionally, the spectroscopic processing means including a plurality of band pass filters, the plural terahertz wave detecting portions being connected to the plural band pass filters, respectively, each band pass filter performing frequency-domain measurement on a detection signal obtained by the corresponding terahertz wave detecting portion to select the desired frequency component, thereby attaining two-dimensional spectroscopic measurement on the sample. Additionally, the excitation light optical system may include an optical chopper controlling on and off of the excitation light at a predetermined driving frequency, the frequency analyzing means detecting, by performing frequency-domain measurement, a frequency component of the detection signal that is determined with respect to the predetermined driving frequency. The frequency analyzing means may include a spectrum analyzer. Or, the frequency analyzing means may include a band pass filter.

The terahertz wave spectrometer according to the present invention can be broadly used in a variety of measurements for measuring the kind, the amount, and the distribution of material in a sample by allowing the sample to affect terahertz wave by causing the terahertz wave to pass through the sample or to reflect off the sample, for example, and then analyzing the frequency of the terahertz wave affected by the sample. It is possible to use any of gases, liquids, and solids as the sample under investigation. It is therefore possible to use the terahertz wave spectrometer according to the present invention broadly in measurements of many kinds of samples, such as of air pollution, exhausted gas, waters semiconductor, and dielectric material.

BRIEF DESCRIPTION OF THE DRAWINGS

The above and other objects, features and advantages of the invention will become more apparent from reading the following description of the preferred embodiments taken in connection with the accompanying drawings in which:

FIG. 1 is a schematic diagram showing the structure of a terahertz wave spectrometer according to a first embodiment of the present invention;

FIGS. 5(A)–5(D) are graphs showing examples of driving waveforms of the movable reflector, wherein FIG. 5(A) shows a triangular wave, FIG. 5(B) shows a trapezoidal wave, FIG. 5(C) shows a sinusoidal wave, and FIG. 5(D) is a sawtooth wave;

FIGS. 9(A) and 9(B) are graphs showing how the frequency spectrum of the detection signal changes in accordance with change of the vibration frequency, wherein FIG. 9(A) shows the frequency spectrum of the detection signal when the vibration frequency is set to 0.5 kHz, and FIG. 9(B) shows the frequency spectrum of the detection signal when the vibration frequency is changed from 0.5 kHz into 0.75 kHz while maintaining the positional amplitude of the vibration unchanged;

FIG. 23(A) is a schematic diagram showing the structure of the terahertz wave spectrometer of FIG. 1 provided with the variable optical delay device including a movable transmitting portion.

DETAILED DESCRIPTION OF THE PREFERRED EMBODIMENTS

Figure 2A:
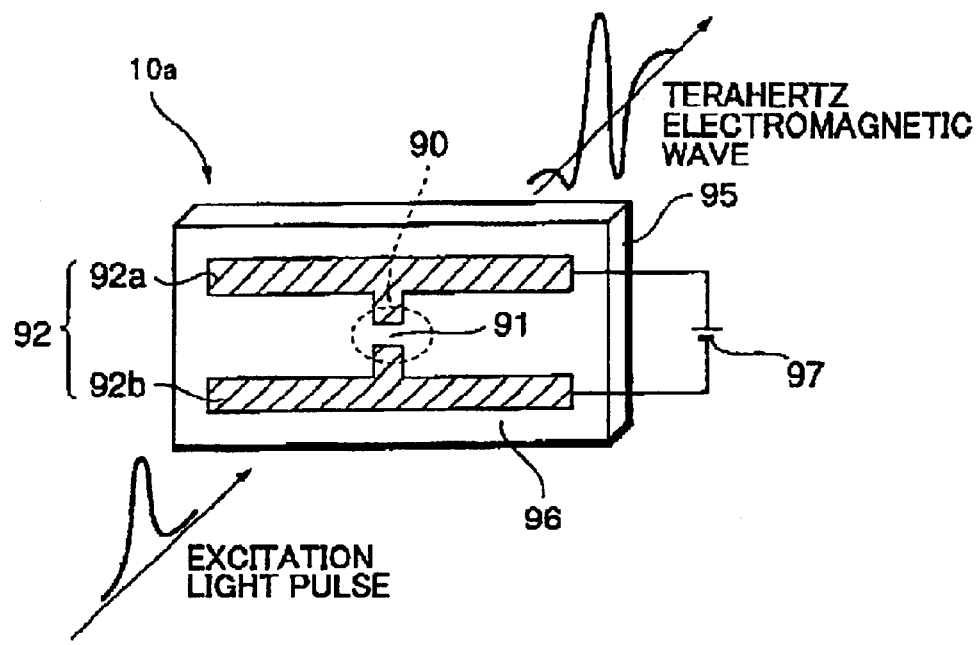
FIG. 2(A) is a schematic diagram illustrating how an optical switching device, which constitutes a terahertz wave generator provided in the terahertz wave spectrometer of FIG. 1, generates a terahertz wave.

Next, a terahertz wave spectrometer according to preferred embodiments of the present invention will be described while referring to FIGS. 1–23(B). Each embodiment is for performing spectroscopic measurement onto a sample to determine the transmission property of the sample.

It should be noted that in the description of the drawings, the same components will be provided with the same reference numerals and duplicate explanation for the same components is omitted. The ratios of sizes appearing in the drawings are not always coincident with the description.

First Embodiment

A terahertz wave spectrometer according to a first embodiment of the present invention will be described with reference to FIGS. 1–7.

FIG. 1 shows the structure of the terahertz wave spectrometer 1 according to the first embodiment of the present invention.

The terahertz wave spectrometer 1 of the present embodiment includes: a predetermined pulse light source 100, a beam splitter 31, an excitation-light optical system 30, a terahertz wave generator 10, a terahertz wave light path 38, a probe-light optical system 35, a terahertz wave detector 20, and a spectroscopic processor 50. The beam splitter 31 is for splitting the light pulse from the pulse light source 100 to generate an excitation light and a probe light. The excitation-light optical system 30 is for guiding the excitation light. The terahertz wave generator 10 is for generating a terahertz wave by using the excitation light guided by the excitation-light optical system 30. The terahertz wave light path 38 is for guiding the terahertz wave to a predetermined sample A, and further for guiding the terahertz wave that has passed through the predetermined sample A. The probe-light optical system 35 is for guiding the probe light. The terahertz wave detector 20 is for detecting the terahertz wave that has passed through the predetermined sample A and that is guided by the terahertz wave light path 38, by using the probe light guided by the probe-light optical system 35, thereby outputting a terahertz wave detection signal. The spectroscopic processor 50 is for processing the detection signal from the terahertz wave detector 20.

As an example of the pulse light source 100, a pulse laser device, such as a femto-second pulse laser, can be used. The excitation-light optical system 30 includes: a reflection mirror 32 and an objective lens 11. The reflection mirror 32 is for changing the direction, in which the excitation light travels. The objective lens 11 is for inputting the excitation light into the terahertz wave generator 10.

According to the present embodiment, an optical switching device 10a, shown in FIG. 2(A), is used as the terahertz wave generator 10. The optical switching device 10a is constructed from a substrate 95 and a photoconductive film or layer 96. The substrate 95 is made of semiconductor, such as GaAs, which has a high speed response. The photoconductive film or layer 96 is made of a low-temperature-grown GaAs, for example, formed on the substrate 95. Parallel transmission lines 92 are formed on the photoconductive film or layer 96. The parallel transmission lines 92 are constructed from a pair of transmission lines 92a and 92b. A single optical switch portion 90 is provided in the center of the parallel transmission lines 92. The optical switch 90 is made from a small dipole antenna. A gap 91 is formed in the center of the optical switching device 10a. The gap 91 has a size of several microns, for example. A proper amount of bias electric voltage is applied through the gap 91 by a direct-current bias power supply 97.

With the above-described structure, the optical switch 10a functions as described below. When a laser pulse light, which has an energy greater than the band gap of the semiconductor, falls incident on the gap 91 as an optical pulse, free carriers are generated in the semiconductor. As a result, an electric current flows in a pulse shape. The pulse-shaped electric current generates a pulse-shaped terahertz wave.

An output lens 12 is provided in the terahertz wave optical path 38 at one side of the optical switch 10a, where the terahertz wave is generated. An off-axis paraboloidal mirror 13 is also provided in the terahertz wave optical path 38. The mirror 13 is for converting the terahertz wave, which has been generated by the terahertz wave generator 10 and which has passed through the output lens 12, into substantially a parallel, collimated light. The predetermined sample A is located in the terahertz wave optical path 38 at such a position that the terahertz wave from the mirror 13 passes through the sample A. The sample A is a target to be measured by the spectrometer. Examples of the sample A include: a cell filled with gas or liquid, and an object.

Another off-axis paraboloidal mirror 23 and an input lens 22 are additionally provided in the terahertz wave optical path 38. The off-axis paraboloidal mirror 23 and the input lens 22 are for inputting the terahertz wave, which has passed through the sample A, onto an optical switching device 20a while focusing the terahertz wave thereon. The optical switching device 20a constitutes the terahertz wave detector 20. The output and input lenses 12 and 22 are made from silicon lenses, for example.

The probe-light optical system 35 is provided with a variable optical delay device 40. The variable optical delay device 40 is for setting (adjusting) difference between the timing of the probe light and the timing of the excitation light. The variable optical delay device 40 includes: a pair of fixed reflection mirrors 41 and 42, a movable reflector 43, and an optical delay controller 44. The optical delay controller 44 is for driving the movable reflector 43 to control its position. By driving (controlling) the position of the movable reflector 43, the optical delay controller 44 can perform control operation to change and set the length of the optical path of the probe light, thereby changing and setting the difference between the excitation light irradiation timing (terahertz wave generating timing) and the probe light irradiation timing (terahertz wave detecting timing).

Another objective lens 21 is further provided in the probe-light optical system 35. The objective lens 21 is for inputting, into the terahertz wave detector 20, the probe light from the variable optical delay device 40.

Figure 2B:
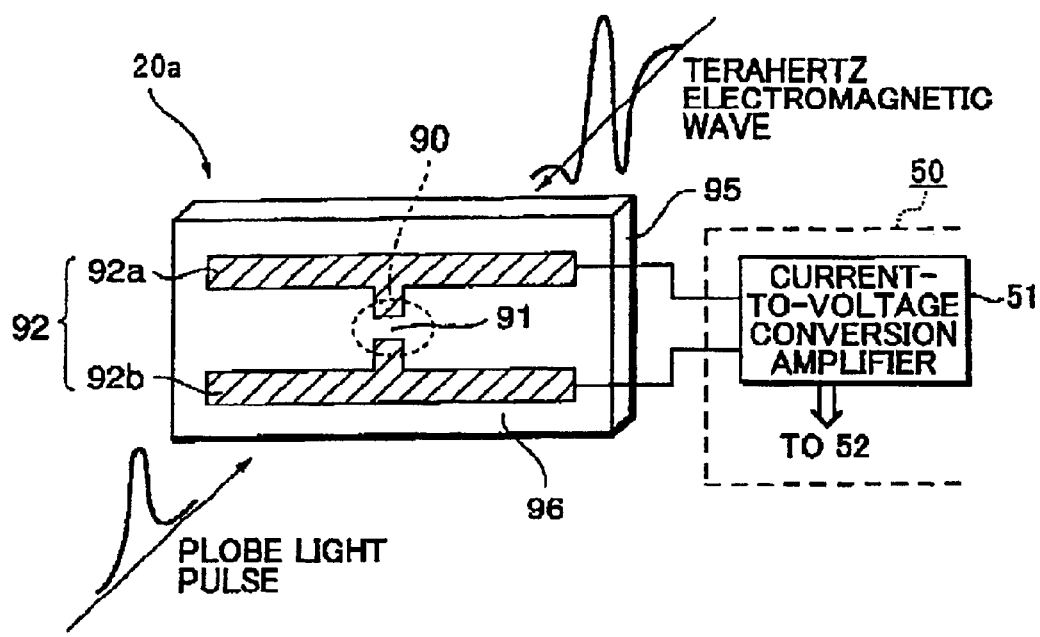
FIG. 2(B) is a schematic diagram illustrating how an optical switching device, which constitutes a terahertz wave detector provided in the terahertz wave spectrometer of FIG. 1, detects a terahertz wave.

The optical switching device 20a, shown in FIG. 2(B), is used as the terahertz wave detector 20. The optical switching device 20a has the same structure as the optical switch 10a. However, the gap 91 of the switching device 20a is not connected to the direct current bias power supply 97, but is connected to the spectroscopic processor 50.

With this structure, the optical switching device 20a functions as described below. The terahertz electromagnetic wave is focused by the input lens 22 onto the dipole antenna 90 on the optical switch 20a. If the probe light pulse from the objective lens 21 excites the gap 91 to generate carriers simultaneously when the terahertz electromagnetic wave falls incident on the dipole antenna 90, an electric current flows to be supplied to the spectroscopic processor 50. The amount of the electric current is proportional to the amplitude of the terahertz electromagnetic wave that reaches the optical switch 20a at the instance that the probe light pulse excites the gap 91.

According to the present embodiment, the spectroscopic processor 50 includes: a current-to-voltage conversion amplifier 51, which is called as the transimpedance amplifier, a spectrum analyzer 52, and an analyzing device 53.

The current-to-voltage conversion amplifier 51 is for converting the current signal, supplied from the switching device 20a, into a voltage signal.

The spectrum analyzer 52 is for performing frequency analysis on the voltage signal, obtained by the current-to-voltage conversion amplifier 51, by determining how power of the voltage signal is distributed at respective frequencies. The spectrum analyzer 52 is constructed from a sweep tuning receiver of a superheterodyne type, for example. The spectrum analyzer 52 sweeps over a target frequency range, and displays amplitudes of signals in all the frequency components included within the frequency range.

Figure 2C:
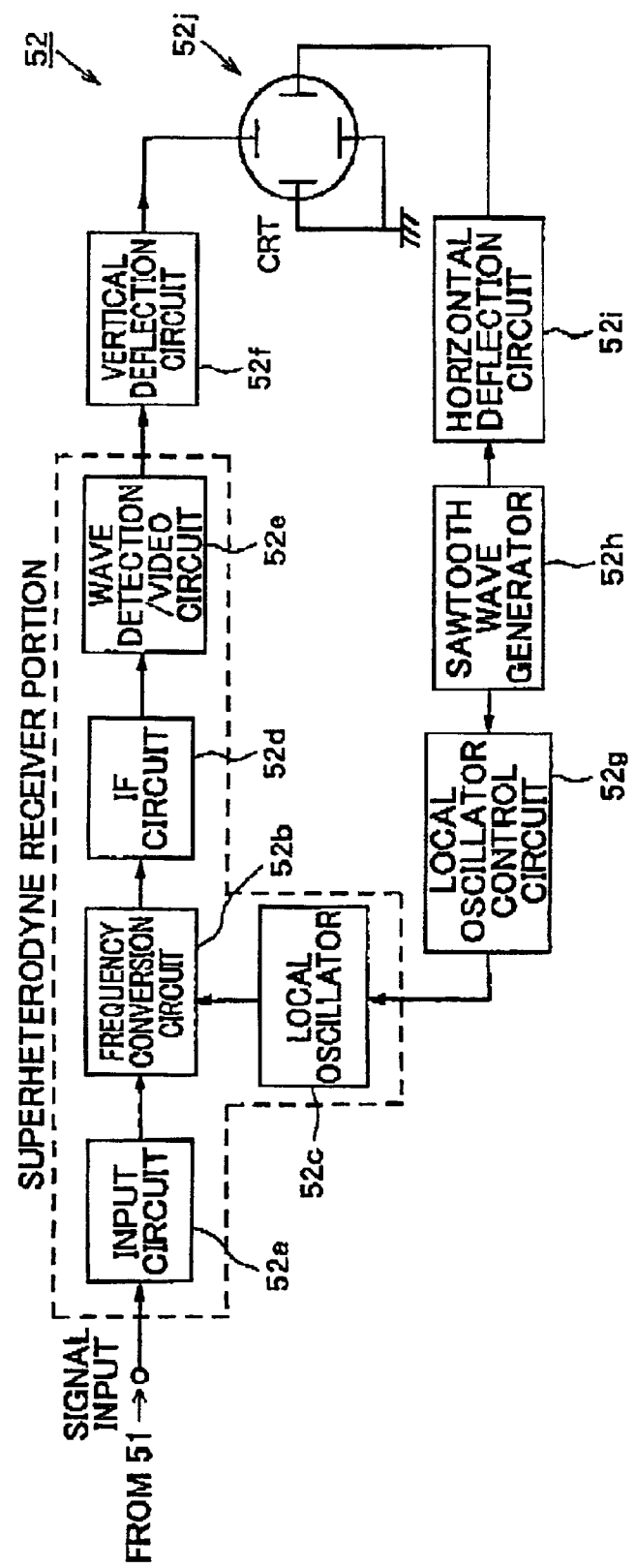
FIG. 2(C) is a block diagram showing the circuit structure of a spectrum analyzer provided in the terahertz wave spectrometer of FIG. 1.

The spectrum analyzer 52 has a structure, as shown in FIG. 2(C), for example. In the spectrum analyzer 52, the detection signal (voltage) from the current-to-voltage conversion amplifier 51 is inputted through an input circuit 52a.

The frequency of the detection signal is converted into a predetermined fixed frequency (intermediate frequency (IF): IF signal) by a frequency conversion circuit 52b and a local oscillator 52c. The thus produced IF signal passes through an IF circuit 52d and a wave detection/video circuit 52e, before being applied, through a vertical deflection circuit 52f, to vertical deflection electrodes of a CRT 52j. It is noted that the input circuit 52a includes an attenuator for adjusting the signal level. The IF circuit 52d includes: a band-pass filter circuit for resolving frequencies; an amplifier; and a logarithmic amplifier. The local oscillator 52c includes a voltage tuned oscillator (VTO) for controlling oscillation frequency by using a voltage.

On the other hand, an output signal, outputted from a sweeping signal generator (sawtooth wave generator) 52h for determining the sweeping time, is supplied via a horizontal deflecting circuit 52i, to the horizontal deflector electrodes of the CRT 52j. The output signal is also supplied, via a control circuit 52g for the local oscillator 52c, to the local oscillator 52c. The local oscillator control circuit 52g includes; a frequency stabilizing circuit; and an attenuator for changing the sweeping width.

With the above-described structure, the spectrum analyzer 52 functions to sweep, with time, the center frequency of a single filter. The spectrum analyzer 52 therefore functions: to divide the input voltage signal into a plurality of sine wave components, to detect each sine wave component and determine its amplitude, to produce a graph indicative of the frequency and the amplitude of each sine wave component, and to quantitatively display the graph on the CRT 52j. In other words, by shifting the center frequency of the single filter with time, the single filter can function as a plurality of band-pass filters, each having a narrow band width. By using the virtual plural filters, the frequency range to be measured is divided into plural frequencies. In this way, the spectrum analyzer 52 displays amplitudes at the respective frequencies. Accordingly, the spectrum analyzer 52 serves to directly analyze the frequency components of the input voltage signal. The spectrum analyzer 52 displays a graph of the amplitude spectrum of the input voltage signal, that is, the relative magnitudes of the respective frequency components in the input voltage signal. The horizontal axis of the graph denotes the frequency level, while the vertical axis denotes the amplitude level.

Instead of using the spectrum analyzer having the above-described structure, a signal spectrum analyzing device disclosed by U.S. Pat. No. 4,257,104, for example, can be used as the spectrum analyzer 52.

The analyzing device 53 is for determining the spectroscopic characteristic of the sample A, which is located in the terahertz wave light path 38, based on the amplitude spectrum obtained by the spectrum analyzer 52. The analyzing device 53 is constructed from a personal computer, or the like. The analyzing device 53 performs calculation operation, which is required to determine the terahertz wave spectroscopic characteristic of the sample A, based on data of the amplitude spectrum obtained by the spectrum analyzer 52. The analyzing device 53 is further provided with a control portion 53a for controlling the optical delay controller 44.

It is noted that the output terminals of the vertical and horizontal deflection circuits 52f and 52i of the spectrum analyzer 52 are connected not only to the CRT 52j, but also to a data bus (general purpose interface bus (GPIB), for example) via an analog-to-digital converter (not shown). The data bus is in turn connected to the analyzing device 53. The analyzing device 53 therefore receives, via the data bus, digital data of the amplitude spectrum from the spectrum analyzer 52. The analyzing device 53 subjects the received digital data to a frequency axis conversion calculation to be described later, thereby determining the terahertz wave spectroscopic characteristic of the sample A. It is noted that if a predetermined portion of the sample A is located in the terahertz wave light path 38 as shown in FIG. 1, the analyzing device 53 determines terahertz wave spectroscopic transmission characteristic of the predetermined portion in the sample A. If the entire portion of the sample A is located in the terahertz wave light path 38, the analyzing device 53 determines terahertz wave spectroscopic transmission characteristic of the entire portion in the sample A.

Next will be described in greater detail the principle how the terahertz wave spectrometer 1 performs spectroscopic measurements.

When the optical path length of the probe light is changed by the variable optical delay device 40, the probe light detection timing changes relative to the input timing when the terahertz wave falls incident on the optical switching device 20a as light to be detected. It is noted that the terahertz wave at frequency of 1 THz has the period of 1 picosecond, which is equivalent to the optical path length of 0.3 mm. Accordingly, if the movable reflector 43 is moved in a direction away from the reflection mirrors 41 and 42 by a distance of 1.5 mm, the optical path length of the probe light is increased by 3 mm, in total, because the probe light travels away from the reflection mirrors 41 and 42 and then back toward the reflection mirrors 41 and 42. As a result, the irradiation timing of the probe light is delayed by 10 picoseconds, in total. This delay time of 10 picoseconds is equivalent to the frequency (step frequency $f_{step}$) of 0.1 THz as determined by the following equation:

Step frequency $f_{step}$ (THz)=(speed of light)/(light-traveling round-trip distance (=3 mm))=1/10 picoseconds=0.1 (THz).

Figure 3A:
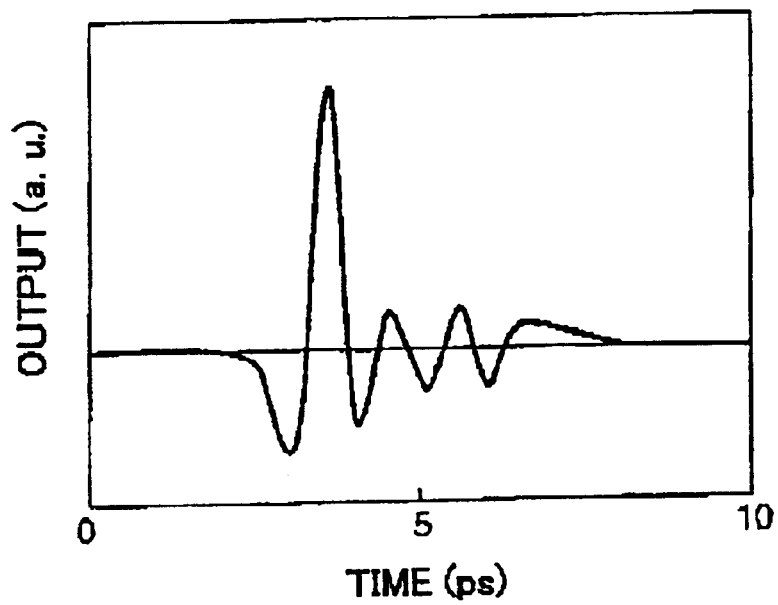
FIG. 3(A) is a graph showing one example of a temporal waveform of the terahertz wave.
Figure 3B:
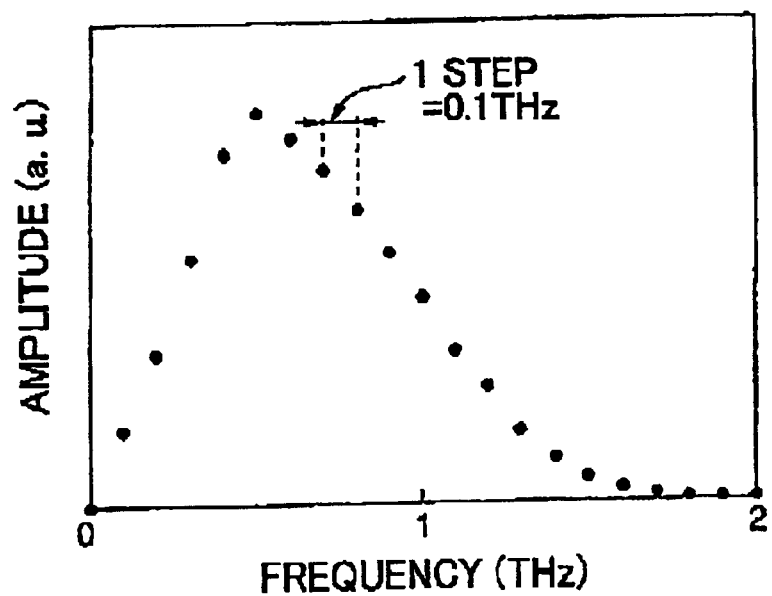
FIG. 3(B) is a graph showing one example of a frequency amplitude spectrum of the terahertz wave.

As a comparative example, it is conceivable that the movable reflector 43 is moved only once in a forward direction in the range of 0 to 3 mm. A time domain measurement is performed to repeatedly perform a terahertz-wave-component measuring operation, while the movable reflector 43 successively reaches the respective positions in the range of 0 to 3 mm and attains the corresponding amounts of delay time. According to this time domain measurement, a temporal waveform of the terahertz wave is obtained as shown in the graph of FIG. 3(A), whose full scale of measurement time (horizontal axis) is 10 picosecond. It is now assumed that data of this temporal waveform is obtained at every 0.1 picosecond/step. In other words, data of the temporal waveform of the terahertz wave of FIG. 3(A) includes 100 data points in total. By subjecting those data points to fast Fourier Transform operation, it is possible to obtain a frequency spectrum, whose full scale is 10 THz, which is equivalent to the data interval of 0.1 picosecond/step. FIG. 3(B) shows a part (range of 0–2 THz) of the thus obtained frequency spectrum with the full scale of 10 THz. In the frequency spectrum, the horizontal axis denotes the frequency and the vertical axis denotes the amplitude of each frequency component. It is noted that the step interval (=step frequency $f_{step}$) between the FFT-calculated points in the spectrum of FIG. 3(B) is 0.1 THz, which corresponds to the full scale of 10 picoseconds in the temporal waveform of FIG. 3(A).

Contrarily, the terahertz wave spectrometer 1 of the present embodiment performs measurements while the variable optical delay device 40 vibrates the optical path length of the probe light at a fixed frequency (fixed period). More specifically, the movable reflector 43 is controlled and driven by the optical delay controller 44 to repeatedly move forward and backward with respect to the reflection mirrors 41 and 42 which are located as being fixed in the variable optical delay device 40.

Figure 4:
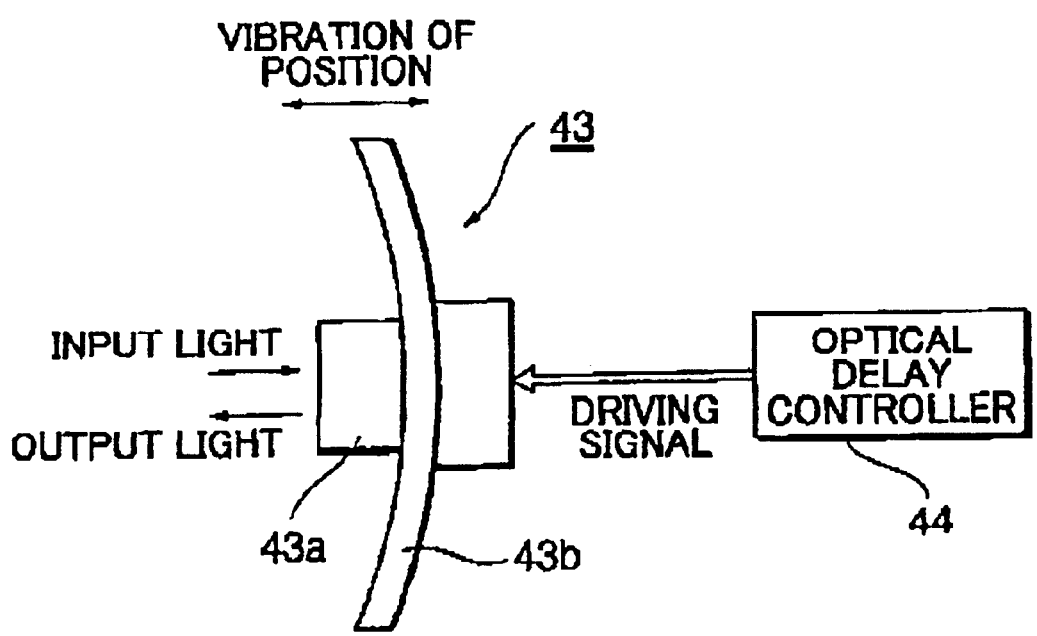
FIG. 4 shows the structure of one example of a movable reflector in a variable optical delay device.

In order to vibrate or periodically change the optical path length at the fixed frequency, the movable reflector 43 is constructed, as shown in FIG. 4. That is, the movable reflector 43 includes a retroreflector 43a, which is fixedly and adhesively attached to a vibrating surface of a speaker 43b. The speaker 43b is an audio speaker for audio devices, for example. The audio speaker 43b vibrates according to driving signals supplied from the optical delay controller 44. With this structure, the location of the retroreflector 43a vibrates in an axial direction, along which the probe light inputs to and outputs from the retroreflector 43a, thereby periodically changing the length of the optical path of the probe light.

It is noted that the amplitude of the positional vibration (the maximum positional change) of the movable reflector 43 is set in correspondence with the full scale of the temporal waveform of the terahertz wave to be detected. For example, the amount of the positional amplitude of the vibration is set in correspondence with the full scale of the measurement time axis that satisfactorily includes the entire waveform of the terahertz wave pulse.

Figure 5A:
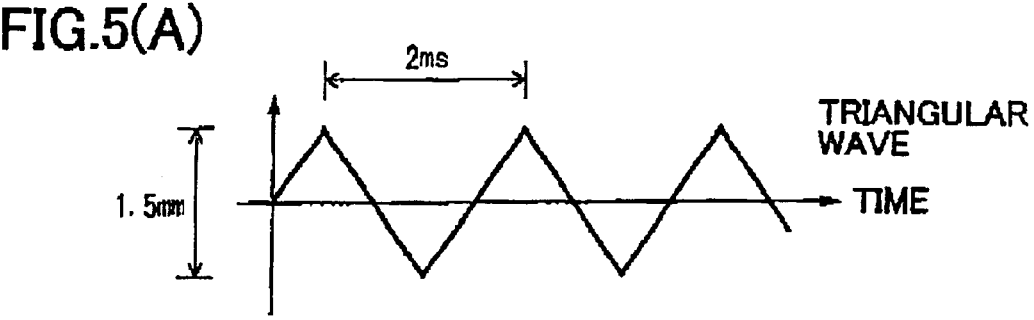
Figure 5B:
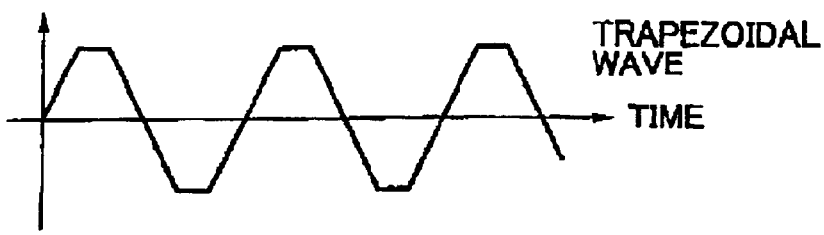
Figure 5C:
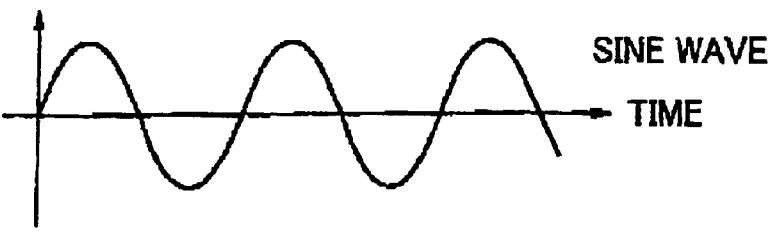
Figure 5D:
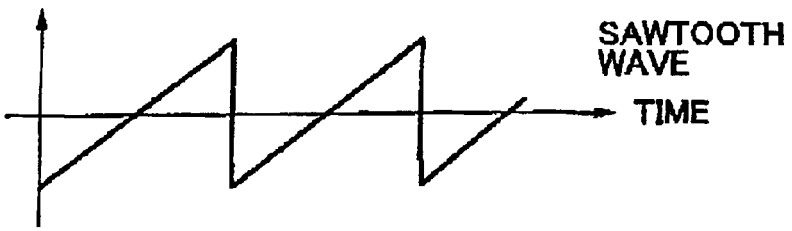

FIGS. 5(A)–5(D) show graphs indicative of representative examples of the temporal waveforms of the driving signals for driving the movable reflector 43. In each graph, the horizontal axis denotes time, and the vertical axis denotes the output of the signal waveform. The signal waveform output in the vertical axis corresponds to the position of the retroreflector 43a that changes in the axial direction of the optical path. The driving waveform in each of FIGS. 5(A)–5(D) has a fixed frequency. FIG. 5(A) shows a triangular wave, FIG. 5(B) shows a trapezoidal wave, FIG. 5(C) shows a sine wave, and FIG. 5(D) shows a sawtooth wave. Any desired waveform can be optionally selected from the waveforms of FIGS. 5(A)–5(D) and other waveforms so that the desired waveform can be driven at a desired frequency by the structure of the movable reflector 43 and so that the desired waveform will be proper for the spectroscopic measurement desired to be conducted. It is especially preferable to select the triangular wave of FIG. 5(A). when the triangular wave is used, the position of the movable reflector 43 changes linearly with time. Accordingly, it becomes unnecessary to perform temporal axis correction operation onto detection signals. Next will be described for the example where the movable reflector 43 is driven by the triangular wave.

According to the terahertz wave spectrometer 1 of the present embodiment, in order to detect and measure the terahertz wave having the temporal waveform of FIG. 3(A), the movable reflector 43 is driven by the triangular wave at frequency of 0.5 kHz to move forward and backward at a vibration positional amplitude (maximum positional change amount) of 1.5 mm. Accordingly, the length of the optical path (probe light traveling distance) changes by 3 mm at maximum. In this case, the temporal waveform of the scanned terahertz wave has the full scale of 10 picoseconds. It is noted that the temporal waveform of the terahertz wave is scanned twice during each period of the triangular wave because the temporal waveform is scanned both in a forward direction and in a backward direction by a single oscillation of the triangular wave. Because the triangular wave has a period of 2 milliseconds, the time period of a single scan is 1 ms, which corresponds to an effective scanning frequency $f_{eff}$=1 kHz (2×0.5 kHz).

Figure 6:
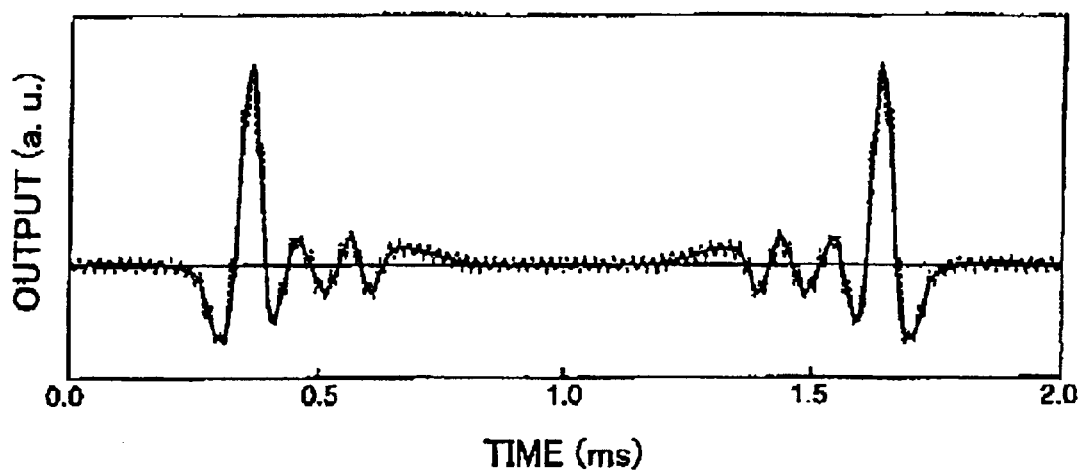
FIG. 6 is a graph showing a temporal waveform of a detection signal, which is obtained by driving in a triangular wave.

In this case, the optical switching device 20a produces a detection signal whose temporal waveform is as shown in FIG. 6. In other words, if the detection signal produced by the optical switching device 20a were subjected to a time domain measurement, a graph as shown in FIG. 6 will be obtained. It is noted that the temporal waveform shown in FIG. 6 corresponds to one period of the triangular wave. The full scale of the temporal waveform is 2 milliseconds, which corresponds to the frequency of 0.5 kHz of the triangular wave. A part of the waveform of FIG. 6 in the time range of 0 to 1 ms has a shape the same as the temporal waveform of the terahertz wave in the full scale of 10 picoseconds in FIG. 3(A), but has its size (full scale) of 1 ms being enlarged from the size (full scale) of 10 picoseconds of the terahertz waveform in FIG. 3(A). The other part of the waveform of FIG. 6 in the time range of 1 to 2 ms has a size enlarged from that of the temporal waveform of FIG. 3(A), but has a shape reversed from that of the temporal waveform of FIG. 3(A). This is because the scanning direction (direction, in which the length of the optical path changes) during the time range of 1 to 2 ms is opposite to the scanning direction during the time range of 0 to 1 ms. It is noted that the triangular wave actually performs oscillation operation, as shown in FIG. 5(A), to successively and continuously oscillate at a fixed frequency. Because the movable reflector 43 is driven by such a triangular wave, the waveform of the detection signal becomes a periodical repetition of the temporal waveform of FIG. 6.

As described above, according to the terahertz wave spectrometer 1 having the structure of FIG. 1, the change in the optical path length, attained by the variable optical delay device 40, corresponds to the change in the detection timing of the terahertz wave. By vibratingly varying the optical path length at a fixed frequency/period, the temporal waveform of the terahertz wave, shown in FIG. 3(A), with the full scale of 10 picoseconds is scale-converted into the temporal waveform of the detection signal, shown in FIG. 6, with the full scale of 1 millisecond.

Figure 7:
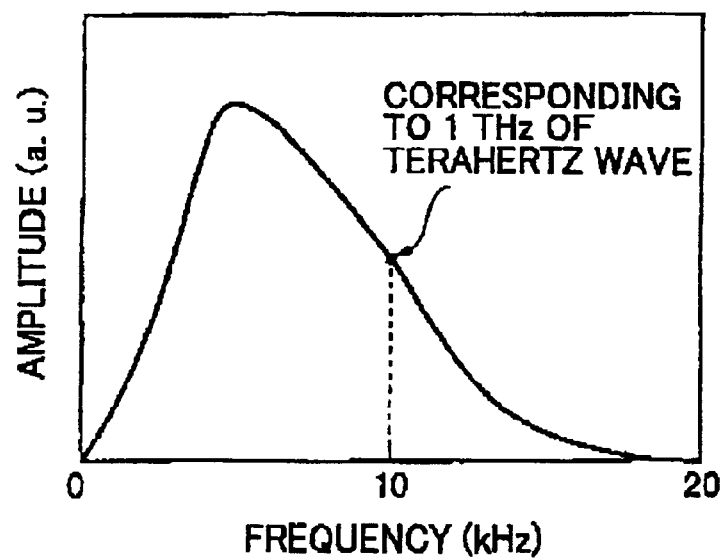
FIG. 7 is a graph showing a frequency spectrum obtained for the detection signal of the temporal waveform of FIG. 6.

According to the present embodiment, the detection signal, whose temporal waveform has a time scale converted in this way, is applied to the spectrum analyzer 52 in the spectroscopic processor 50. That is, the thus scale-converted detection signal is inputted to the spectrum analyzer 52. The spectrum analyzer 52 serves as a frequency analyzer. That is, the spectrum analyzer 52 performs frequency analysis on the temporal waveform of the inputted signal, and produces a frequency spectrum of the signal. Accordingly, the spectrum analyzer 52 directly obtains a frequency spectrum, as shown in FIG. 7, based on the detection signal having the temporal waveform of FIG. 6. If the thus obtained frequency spectrum is indicated in the full scale of 20 kHz as shown in FIG. 7, the frequency spectrum of FIG. 7 has the same shape with that of the frequency spectrum of FIG. 3(B), which is obtained by the fast Fourier transform operation and which has the full scale of 2 THz. Thus, the frequency spectrum of FIG. 7 has the same shape with the frequency spectrum of FIG. 3(B), but has its scale converted from the scale of the frequency spectrum of FIG. 3(B).

In this way, by vibrating the optical path length at the frequency of 0.5 kHz, the frequency component of 1 THz in the frequency spectrum of the terahertz wave is scale-converted into the frequency component of 10 kHz in the frequency spectrum of the detection signal.

It is noted that the following formula (1) represents the relationship between the frequency value f (THz) of the terahertz wave and the frequency value $f_{spec}$ (kHz), defined on the frequency axis of the frequency spectrum obtained by the spectrum analyzer 52:

$$f(THz) = f_{spec}(kHz) \times f_{step}(THz)/f_{eff}(THz) \quad (1).$$

wherein the step frequency $f_{step}$ (THz) and the effective scanning frequency $f_{eff}$ satisfy the following equations:

step frequency $f_{step}$(THz)=(speed of light)/(optical path length vibrating amplitude of×2)

effective scanning frequency $f_{eff}$(kHz)=(optical path length vibrating frequency)×2

In the example where the optical path length vibrating amplitude is 1.5 mm and the optical path length vibrating frequency is 0.5 kHz, the step frequency $f_{step}$ (THz) has a value of 0.1 THz (=(speed of light)/(1.5 mm×2)), and the effective scanning frequency $f_{eff}$ (kHz) has a value of 1 kHz (=0.5 kHz×2).

By calculating 1 (THz)=10 (kHz)×0.1 (THz)/1 (kHz), it is known that the frequency value $f_{spec}$ (kHz) of 10 kHz, obtained at the spectrum analyzer 52, corresponds to the terahertz wave frequency f (THz) of 1 (THz). It is noted that because the triangular wave causes the optical path length to change linearly with time, frequency values of the terahertz waves other than the above-described value, are also linearly scale-converted into the frequency values at the spectrum analyzer 52.

In this way, the variable optical delay device 40 vibratingly changes the optical path length of the probe light at the fixed frequency/period, thereby vibratingly changing the probe light irradiation timing. It is therefore possible to obtain a detection signal, whose temporal waveform has the same shape with that of the terahertz wave but has time and frequency scale-converted from the time and frequency of the terahertz wave. By applying such a detection signal to the spectrum analyzer 52, which serves as a frequency analyzer in the spectroscopic processor 50, it is possible to directly obtain the frequency spectrum, without performing any fast Fourier transform operation. The thus obtained frequency spectrum has the same shape with the frequency spectrum of the terahertz wave, but has its frequency scale-converted from that of the original frequency spectrum of the terahertz wave.

It is noted that the controller 53a in the analyzer 53 is connected to the optical delay controller 44. The controller 53a can set, to desired values, the frequency fs and the amplitude, at which the optical path length of the probe light should be vibrated. In this example, the controller 53a sets the frequency fs to 0.5 kHz and the amplitude to 1.5 mm. The optical delay controller 44 vibrates the movable reflector 43 at the frequency and amplitude set by the controller 53a, thereby vibrating the probe light optical path length. As a result, the spectrum analyzer 52 produces the amplitude spectrum as shown in FIG. 7.

The spectrum analyzer 52 produces the amplitude spectrum, and outputs data of the amplitude spectrum to the analyzer 53. The analyzer 53 performs calculations to attain scale-conversion of the frequency axis in the frequency spectrum. Because the frequency axis of the amplitude spectrum, obtained by the spectrum analyzer 52, is in the order of kilohertz (kHz), the analyzer 53 performs calculations to scale-convert the frequency axis from the order of kilohertz (kHz) into the order of terahertz (THz) of the original frequency of the terahertz wave. For example, the analyzer 53 performs the scale-conversion calculation by using the above-described formula (1) and by using the values of the vibrating frequency and the vibrating amplitude (maximum moving amount) of the movable reflector 43, which are set by the controller 53a. The analyzer 53 can further convert the frequency axis into the wavelength axis by calculating the formula of c=f·λ (wherein c=speed of light, f is frequency, λ is wavelength). The amplitude spectrum, obtained through the above-described calculation, indicates the spectroscopic transmission property of the sample A, and accordingly indicates the physical and chemical information of the sample A.

With the above-described structure, the terahertz wave spectrometer 1 operates as described below.

The optical pulse from the pulse light source 100 is split by the beam splitter 31 to generate: an excitation light to be irradiated onto the terahertz wave generator 10 and a probe light to be irradiated onto the terahertz wave detector 20. In the excitation light optical path 30, the reflection mirror 32 changes the traveling direction of the excitation light into the predetermined direction. The excitation light falls incident on the optical switching device 10a via the objective lens 11. The optical switching device 10a constitutes the terahertz wave generator 10. When the excitation light falls incident on the gap 91 of the optical switching device 10a as an optical pulse, terahertz wave is generated in a pulse form.

In the terahertz wave optical path 38, the terahertz wave passes through the output lens 12, and is converted by the off-axis paraboloidal mirror 13 into substantially a parallel, collimated light. The terahertz wave then passes through the sample A. The terahertz wave falls incident on the optical switching device 20a while being focused thereon by the off-axis paraboloidal mirror 23 and the input lens 22. The optical switching device 20a constitutes the terahertz wave detector 20.

In the probe light optical path 35, the probe light, which has been separated by the beam splitter 31 from the excitation light, falls incident on the optical switching device 20a via the objective lens 21, while the difference of the irradiation timing of the probe light from the irradiation timing of the excitation light is vibratingly varied by the variable optical delay device 40. In this way, detection of the terahertz wave is conducted by irradiating the probe light onto the optical switching device 20a while synchronizing the probe light irradiation timing with the excitation light irradiation timing with the difference therebetween vibratingly changing. As a result, the detection signal (electric current) outputted from the optical switching device 20a has the temporal waveform as shown in FIG. 6. The temporal waveform of the detection signal has the same shape with that of the original terahertz wave shown in FIG. 3(A), and has the time scale converted from that of the terahertz wave. The detection signal (electric current) is converted into a voltage signal by the current-to-voltage conversion amplifier 51, and is inputted into the spectrum analyzer 52. As a result, the amplitude spectrum shown in FIG. 7 is generated. The thus generated amplitude spectrum has the same shape with that of the terahertz wave of FIG. 3(B) and has the frequency scale converted from that of the terahertz wave of FIG. 3(B). The analyzer 53 performs predetermined data processing, such as a frequency axis conversion, onto the spectrum data of the detection signal, thereby obtaining spectrum data indicative of the spectroscopic transmission characteristic of the sample A.

In this way, according to the terahertz wave spectrometer 1 of the present embodiment, it is ensured that the terahertz wave spectroscopic measurement is performed in real time. The device/circuit structure is simplified, and the cost required to produce the entire device is reduced, thereby making the device less costly. By simplifying the circuit structure, the device can be assembled into an integrated circuit construction. It is possible to effectively apply the present embodiment to simplify the structure of the spectrometer and to use the spectrometer to various measurements.

It is noted that the output signals from the current-to-voltage amplifier 51 are generally mixed with noise signals as indicated by dotted line in FIG. 6. This leads to decrease of the signal-to-noise ratio, which in turn decreases the accuracy of the spectroscopic measurements. To solve this problem, the bandwidth (frequency range (sweeping frequency range)) of the spectrum analyzer 52 may be set into a narrower range, thereby increasing the signal-to-noise ratio.

There will be the case where the sample A has some special transmission property, and therefore a user desires to observe a specific frequency-range component or a specific frequency component within the frequency spectrum of the terahertz wave. In this case, the user will desire to perform spectroscopic measurement by detecting intensity at the specific frequency or specific frequency-range. Such a spectroscopic measurement becomes possible by limiting the measurement frequency range of the spectrum analyzer 52 only to the specific frequency range or by setting the spectrum analyzer 52 to a predetermined measurement mode (zero-span mode) to measure the specific frequency only. During the zero-span mode, the frequency sweeping span of the spectrum analyzer 52 is set to zero (0) Hz. Accordingly, the spectrum analyzer 52 functions as a receiver whose frequency is fixed to the specific frequency. The spectrum analyzer 52 will measure and display the temporal change in the amplitude of the sine wave component at the specific frequency.

For example, when it is desired to observe the frequency component of 1 THz within the frequency spectrum in FIG. 3(B) of the terahertz wave, the spectrum analyzer 52 is set to the zero-span mode in order to measure the frequency component of 10 kHz in the frequency spectrum in FIG. 7 of the detection signal. As a result, it becomes possible to perform continuous measurement onto the terahertz wave component of 1 THz. By performing the measurement while moving the sample A two-dimensionally under this measurement condition, it is possible to attain a two-dimensional imaging of the sample. When it is desired to change, into 2 THz, the frequency component of the terahertz wave to be observed, the measurement condition can be changed by merely changing, into 20 kHz, the measurement frequency at the zero-span mode in the spectrum analyzer 52. It is noted that the two-dimensional imaging performed by the terahertz wave spectrometer will be described later.

As described above, according to the terahertz wave spectrometer 1 of the present embodiment, the movable reflector 43 in the variable optical delay device 40 is driven at the predetermined frequency, thereby vibrating the timing when the probe light is irradiated onto the optical switching device 20a in the terahertz wave detector 20. The optical switching device 20a detects the terahertz wave that has been emitted from the terahertz wave generator 10 and that has passed through the sample A, and outputs a detection signal, which vibratingly changes periodically. The detection signal is subjected to a frequency analysis by the spectrum analyzer 52 in the spectroscopic processor 50. The detection signal has a temporal waveform, whose shape is the same as that of the terahertz wave that is affected by the sample A by passing through the sample A, and whose scale is converted from that of the terahertz wave. It is therefore possible to perform real-time frequency analysis onto the terahertz wave, per se. by performing frequency analysis on the detection signal.

As described above, according to the terahertz wave spectrometer 1 of the present embodiment, first of all, the variable optical delay device 40 vibratingly changes the irradiation timing of the probe light so that the irradiation timing periodically and continuously changes (scans) at the predetermined frequency. This enables converting the time scale of the temporal waveform of the terahertz wave and the frequency scale of the frequency spectrum of the terahertz wave into time scale and frequency scale that can be easily processed directly.

Secondly, the frequency analyzing device, such, as the spectrum analyzer 52, is employed to perform a frequency spectrum measurement on the terahertz wave by measuring the detection signal, whose temporal waveform has time-scale converted from that of the original terahertz wave but has its shape exactly the same with or quasi-same with that of the terahertz wave, and whose frequency spectrum has frequency-scale converted from that of the original terahertz wave but has its shape exactly the same with or quasi-same with that of the terahertz wave. Accordingly, it is unnecessary to use devices for performing FFT calculation, analog-to-digital converters, or digital signal processors (DSPs). It is possible to perform real-time measurement by using a simplified device structure. It is possible to set the spectrum analyzer 52 under various types of measurement conditions, including a condition for detecting a narrow bandwidth. Accordingly, it is possible to perform high quality spectroscopic measurement with an enhanced signal-to-noise ratio.

Second Embodiment

Next, a terahertz wave spectrometer according to a second embodiment of the present invention will be described with reference to FIGS. 8(A)–9(B).

Figure 8A:
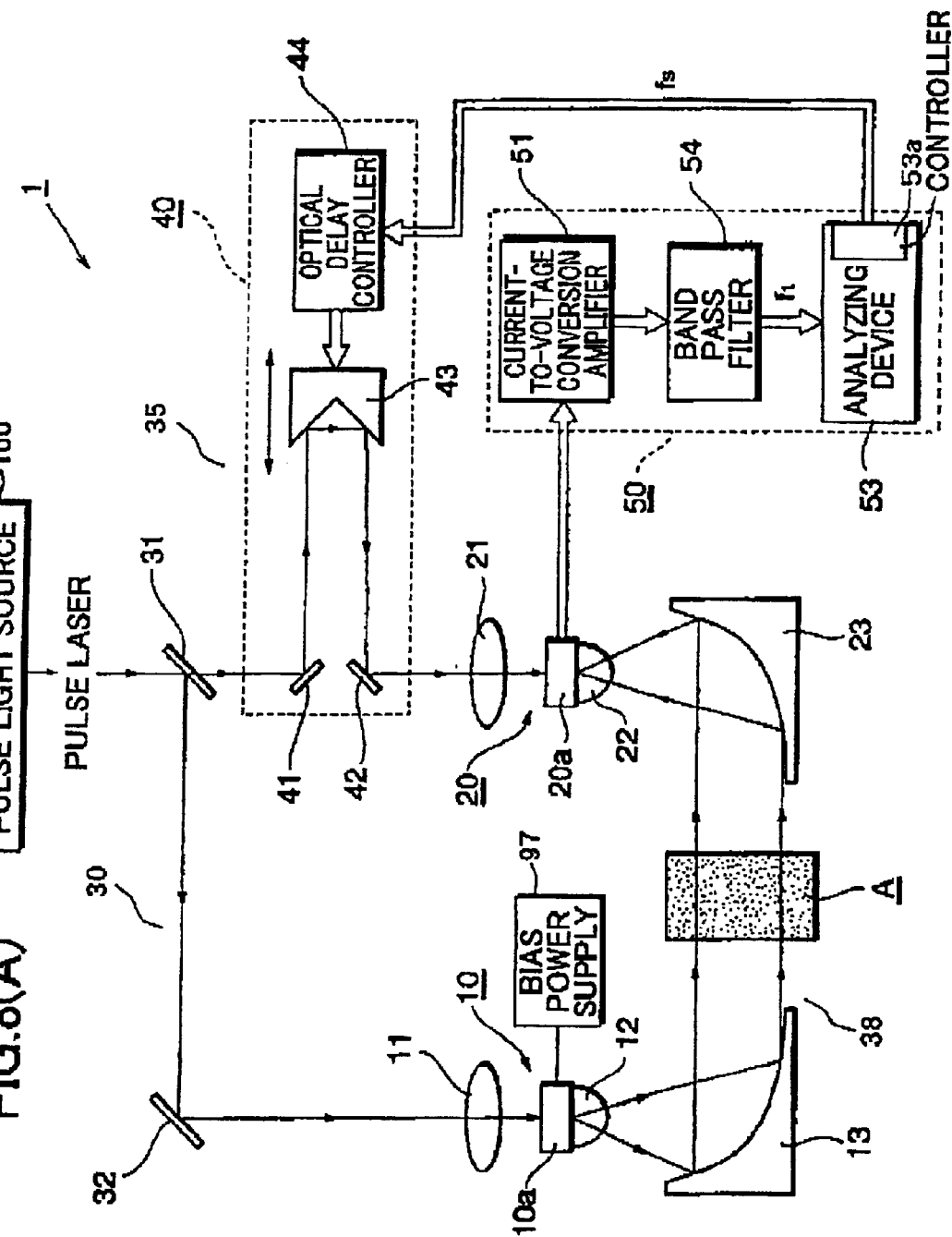
FIG. 8(A) is a schematic diagram showing the structure of a terahertz wave spectrometer according to a second embodiment.

FIG. 8(A) shows the structure of the terahertz wave spectrometer 1 according to the second embodiment of the present invention. The same or equivalent portions as those in the terahertz wave spectrometer 1 of the first embodiment are indicated by the same reference numerals, and description of these portions are omitted.

The present embodiment employs the terahertz wave generator 10, the terahertz wave detector 20, and the optical systems 30, 35, and 38, in the same manner as in the first embodiment. However, according to the present embodiment, the spectroscopic processor 50 employs a band-pass filter 54, instead of using the spectrum analyzer 52. The band-pass filter 54 has a narrow-band, and serves as a frequency analyzer for analyzing frequency of the detection signal.

In the first embodiment employed with the spectrum analyzer 52, as described above, when it is desired to perform a spectroscopic measurement on the terahertz wave of some specific frequency (target frequency), it is possible to attain such a measurement by setting the measurement mode of the spectrum analyzer 52 into the zero-span mode to measure only the frequency component of the detection signal that corresponds to the target frequency. When the target frequency f1 is previously known, instead of using the spectrum analyzer 52, it is possible to use the band-pass filter 54 as described below in the present embodiment. The band-pass filter 54 is of a narrow-band type, for example, that can select the target frequency f1 component.

By using the band-pass filter 54, in comparison with using the spectrum analyzer 52, it is possible to further simplify the entire device and to produce the device less costly. It becomes possible to more easily assemble the device into an integrated-circuit construction.

Figure 8B:
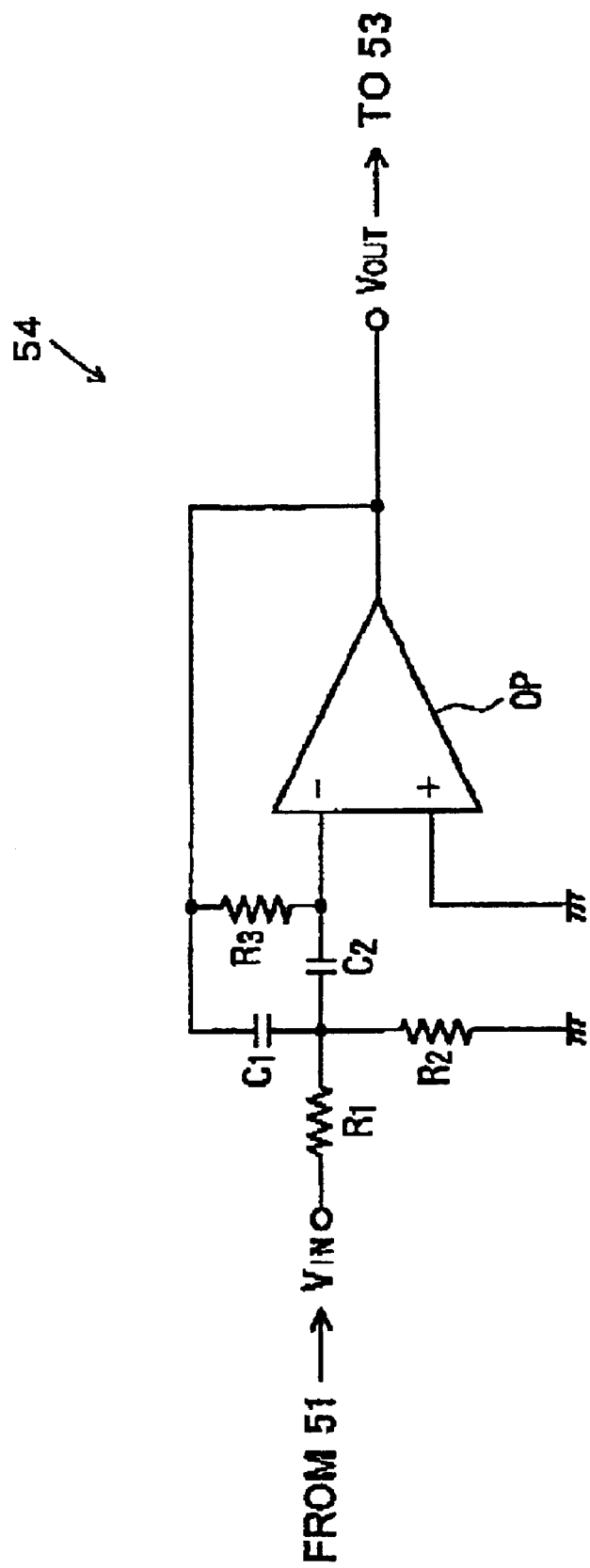
FIG. 8(B) is a circuit diagram showing an example of a band-pass filter 54 provided in the terahertz wave spectrometer of FIG. 8(A)

The band-pass filter 54 can be made in the form of an active filter that employs an operational amplifier (OP amplifier). In this case, the band-pass filter 54 can easily attain high resonance characteristics. For example, as shown in FIG. 8(B), the band-pass filter 54 can be constructed from: an operational amplifier OP;1 and resistors R1, R2, and R3 and capacitors C1 and C2 which serve as passive elements. A detection signal (voltage) from the current-to-voltage conversion amplifier 51 is inputted to the input terminal $V_{IN}$ of the band-pass filter 54. Receiving the thus inputted detection signal, the band pass filter 54 outputs, via the output terminal $V_{OUT}$, only a signal with a frequency that is determined by the resistance values of the resistors R1, R2, and R3 and the capacitance values of the capacitors C1 and C2.

In the present embodiment, the output terminal $V_{OUT}$ of the band-pass filter 54 is connected to the analyzing device 53 via an analog-to-digital (A/D) converter (not shown). With this structure, the output signal from the output terminal $V_{OUT}$ is subjected to an analog-to-digital conversion, and the resultant digital numerical value data is inputted into the analyzing device 53. The digital numerical value data is indicative of the intensity of the terahertz wave at a frequency component that corresponds to the frequency of the detection signal selected by the band-pass filter 54. In other words, the digital numerical value data indicates the spectroscopic characteristic of the predetermined sample A with respect to the target frequency component of the terahertz wave. The analyzing device 53 performs predetermined data processing operation, such as a calculation operation to convert the frequency value selected by the band-pass filter 54 into the corresponding frequency value of the terahertz wave, and then to convert the calculated result further into the wavelength value. As a result, it is possible to obtain spectroscopic data indicative of how terahertz wave of the predetermined frequency is transmitted through the sample A. The thus obtained spectroscopic transmission characteristic data is indicative of physical and chemical information of the sample A.

It is noted that the band-pass filter 54 may be constructed from: resistors R, capacitors C, and inductors L, all of which are passive elements, only.

Additionally, by controlling the driving conditions of the variable optical delay device 40, it is possible to set or change the frequency value of the target component among a plurality of different components of the terahertz wave. In order to attain this object, the controller 53a in the analyzing device 53 is constructed so as to be capable of changing and setting the frequency fs, at which the variable optical delay device 40 vibrates the probe light optical path length.

Figure 9A:
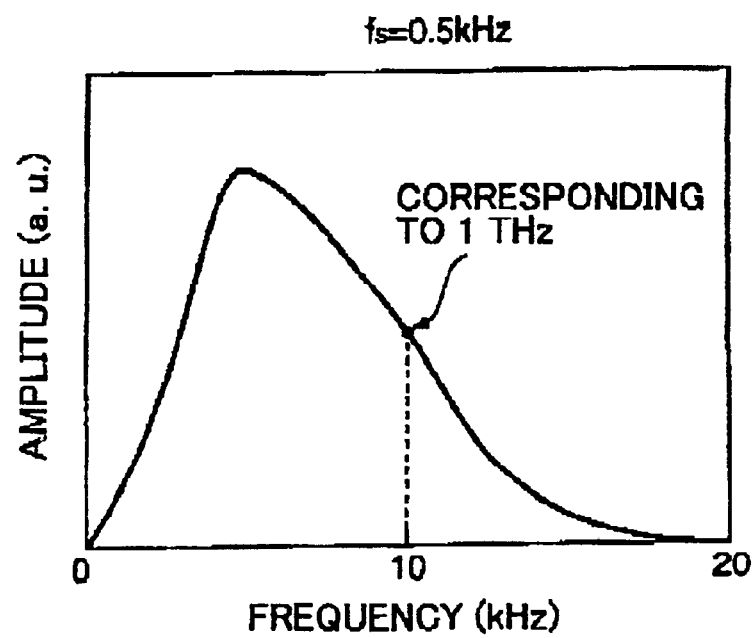
Figure 9B:
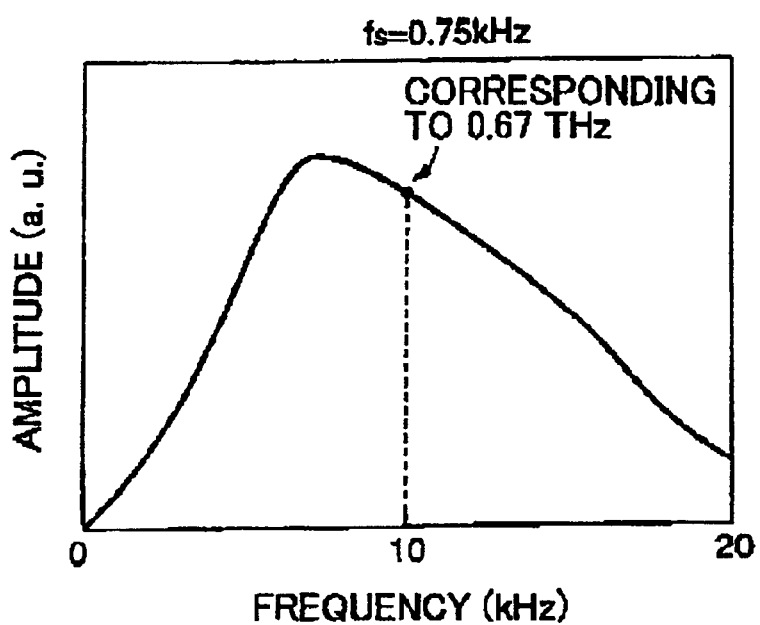

FIGS. 9(A)–9(B) show how the frequency spectrum of the detection signal, obtained by the terahertz wave detector 20, changes according to the change of the vibrating frequency fs of the probe light optical path length. FIG. 9(A) shows the frequency spectrum of the detection signal, which is obtained when the vibration frequency fs at the variable optical delay device 40 is set to fs=0.5 kHz. This frequency spectrum is therefore the same as that shown in FIG. 7. The frequency 10 kHz of the detection signal corresponds to the frequency component 1 THz of the terahertz wave. If the vibration frequency fs is changed from 0.5 kHz into 0.75 kHz while keeping unchanged the vibration positional amplitude (maximum movement amount), the frequency spectrum of the detection signal changes from FIG. 9(A) into FIG. 9(B). The frequency 10 kHz of the detection signal now corresponds to the frequency component 0.67 THz of the terahertz wave.

According to the present embodiment, the band-pass filter 54 has a fixed structure, and can therefore measure (select) frequency of some fixed predetermined value, for example, 10 kHz, of the detection signal. According to the present embodiment, therefore, the controller 53a is constructed so as to be capable of controlling the frequency, at which the variable optical delay device 40 vibrates the probe light optical path length, that is, the irradiation timing. By changing the vibration frequency fs, it is possible to change the correspondence relationship between the frequency scale of the detection signal frequency spectrum and the frequency scale of the terahertz wave frequency spectrum, without replacing the band-pass filter 54 with a different one. For example, by changing the vibration frequency fs from 0.5 kHz into 0.75 kHz as described above, it is possible to change the target frequency of the terahertz wave from 1 THz into 0.67 THz.

It is noted that the analyzing device 53 performs calculation to convert the frequency value of the detection signal, selected by the band-pass filter 54, into the target frequency value of the terahertz wave, by using the value of the vibration frequency fs which is changed and set by the controller 53a. The intensity of the detection signal, at the frequency corresponding to the target frequency of the terahertz wave, indicates the spectroscopic characteristics of the sample B at the target frequency.

It is also noted that the target frequency can be changed also in the device structure of the first embodiment that employs the spectrum analyzer 52. More specifically, in the first embodiment, the controller 53a may change the frequency fs, at which the variable optical delay device 40 vibrates the optical path length. It is therefore possible to freely change the measurement target frequency component among the plurality of frequency components of the terahertz wave.

Third Embodiment

Next, a terahertz wave spectrometer according to a third embodiment of the present invention will be described with reference to FIG. 10.

Figure 10:
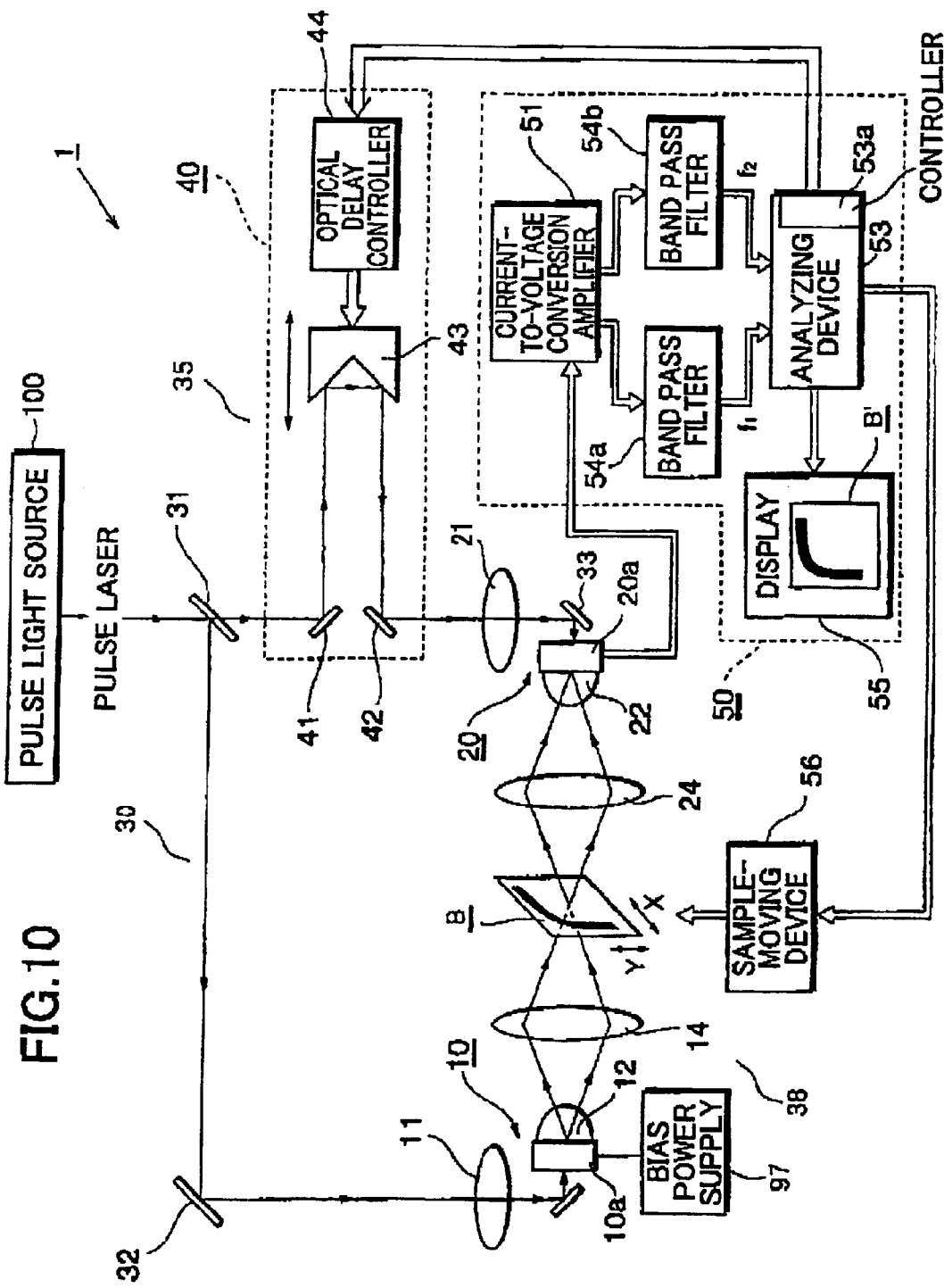
FIG. 10 is a schematic diagram showing the structure of a terahertz wave spectrometer according to a third embodiment of the present invention.

FIG. 10 shows the structure of the terahertz wave spectrometer 1 according to the third embodiment of the present invention. The same or equivalent portions as those in the terahertz wave spectrometer 1 of the first embodiment are indicated by the same reference numerals, and description of these portions are omitted, The present embodiment employs the excitation-light optical system 30 in the same manner as the first embodiment. The present embodiment employs the optical switching devices 10a and 20a as the terahertz wave generator 10 and the terahertz wave detector 20 as in the first embodiment. However, in the probe-light optical system 35, a reflective mirror 33 is additionally provided in the rear side of the objective lens 21. The reflective mirror 33 is for changing the direction in which the probe light travels. In the terahertz wave optical system 38, the off-axis paraboloidal mirror 13 or 23 is not provided, but the optical switching devices 10a and 20a are located as opposing to each other.

The terahertz wave, emitted from the optical switching device 10a (terahertz wave generator), passes through the output lens 12 in the terahertz wave optical system 38. The terahertz wave is irradiated on the sample B, while being focused by a focusing lens 14 onto one position on the sample B, and passes through the sample B. The terahertz wave is then collected and focused by the other focusing lens 24, passes through the input lens 22, and falls incident on the optical switching device 20a (terahertz wave detector). By constructing the terahertz wave optical system 38 in the structure described above, it is possible to perform a spectroscopic measurement on a specific portion of the sample B.

Additionally, according to the present embodiment, a sample-moving device 56 is provided to two-dimensionally move the sample B in an X–Y plane that is substantially perpendicular to the optical axis of the terahertz wave. The sample-moving device 56 is controlled by the analying device 53 in the spectroscopic processor 50. By moving the sample B so that the respective two-dimensional positions on the sample B will successively be located as a portion to be measured, it is possible to scanningly measure the sample B, and to attain a two-dimensional spectroscopic imaging. According to the present embodiment, a display device 55, such as a display screen, is connected to the analyzing device 53 and displays an image of the measured result of the two-dimensional imaging. The thus obtained two-dimensional imaging resultant image indicates the two-dimensional distribution information of the physical and chemical characteristics of the sample B.

It is noted that the spectrum analyzer 52 or the band-pass filter 54 described above can be used as the frequency analyzing device in the spectroscopic processor 50. In the example shown in FIG. 10, two band-pass filters 54*a* and 54*b* are used as the frequency analyzing device. The band-pass filters 54*a* and 54*b* are capable of selecting components of frequencies f1 and f2 which are different from each other.

For example, it is assumed that it is desired to spectroscopically measure how some material is distributed in the sample B. It is also assumed that the subject material characteristically absorbs terahertz wave of some frequency that corresponds to frequency f1 of the detection signal and absorbs little terahertz wave of another frequency that corresponds to frequency f2 of the detection signal. In this case, it is possible to efficiently determine the distribution of the material precisely, by first measuring the transmission characteristics at both of the frequencies f1 and f2 and then determining the correlation of the two transmission characteristics by calculating the difference or the product of the two transmission characteristics. A two-dimensional image B' indicative of the distribution of the material in the sample B is obtained, and displayed on the display device 55, such as the display screen, connected to the analyzing device 53.

More specifically, with respect to each position on the sample B, the transmission characteristic at frequency f1 is measured by the band-pass filter 54*a*, while the transmission characteristic at frequency f2 is measured by the band-pass filter 54*b*. The analyzing device 53 is connected to the band-pass filters 54*a* and 54*b* via an analog-to-digital converter (not shown), and obtains the analog-to-digital converted values of the output signals from the band-pass filters 54*a* and 54*b*. The analyzing device 53 calculates the correlation value (difference or product, for example) between the thus obtained two digital values. The analyzing device 53 further performs, based on the positional information of the sample B, processing operations required to display the image of the correlation value, and outputs the processed results to the display device 55. The display device 55 displays, based on the results processed by the analyzing device 53, a two-dimensional spectroscopic image B' which is indicative of how material is distributed in the sample B.

By thus performing the measurement operation and the comparison operation with respect to the plurality of frequency components, it is possible to obtain more detailed information on the sample. In this case, the present embodiment is not limited to the case where two band-pass filters are used. When necessary, it may be possible to employ three or more band-pass filters for three or more different frequencies. The device of the present embodiment may be modified to perform spectroscopic analyzing operation based on a correlation result of the measurement data obtained from those three or more band-pass filters. Alternatively, the device of the present embodiment may be modified so as to use the spectrum analyzer 52 as the frequency analyzing device and to perform the processings (analyzing operations) in the similar manner as described above. That is, after determining the frequency spectrum by the spectrum analyzer 52, the analyzing device 53 is controlled to select a plurality of frequency ranges from the frequency spectrum. Then, the correlation among the transmission characteristics at the selected plural frequency ranges is determined Fourth Embodiment Next, a terahertz wave spectrometer according to a fourth embodiment of the present invention will be described with reference to FIGS. 11–12(B).

Figure 11:
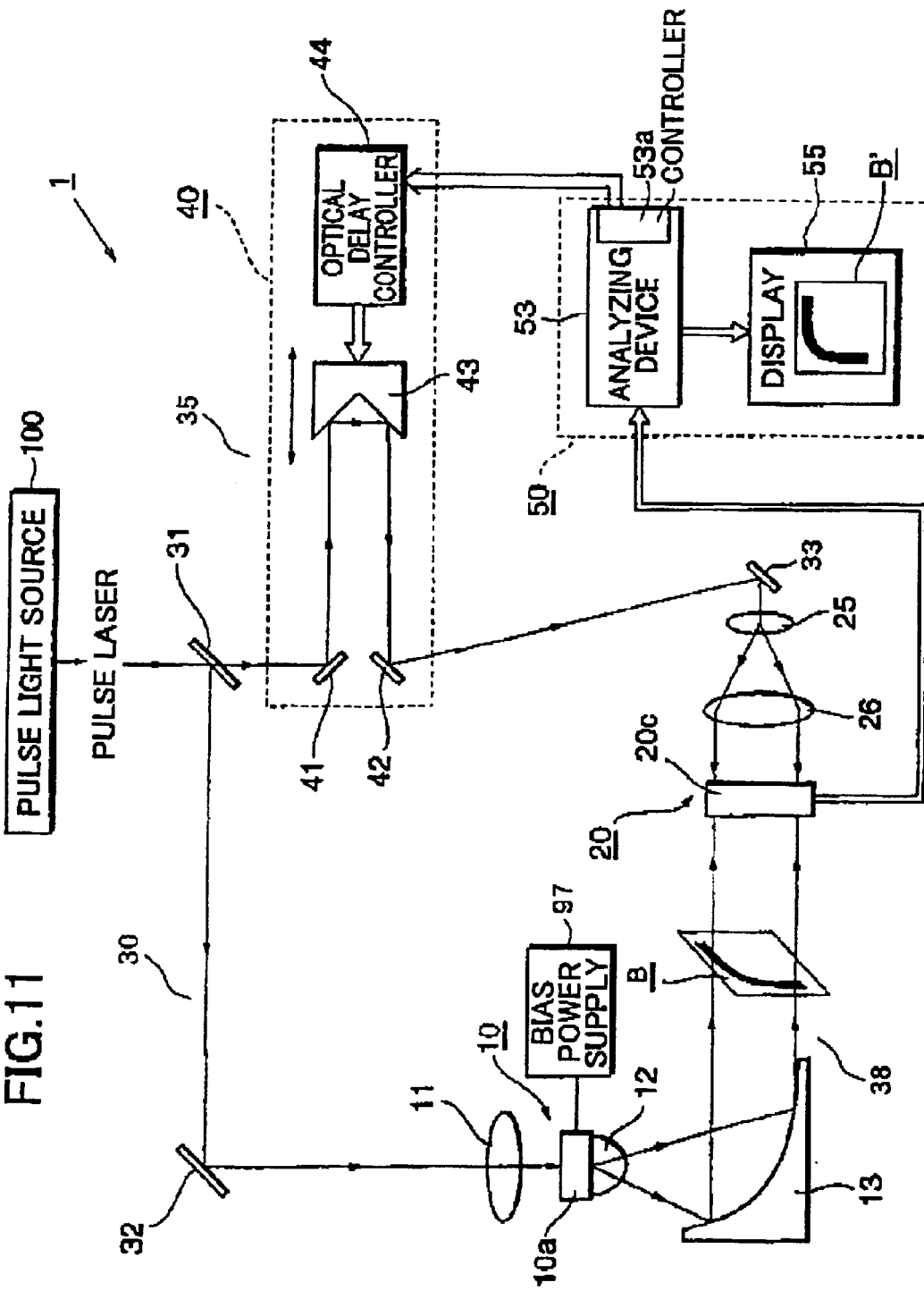
FIG. 11 is a schematic diagram showing the structure of a terahertz wave spectrometer according to a fourth embodiment of the present invention.

FIG. 11 shows the structure of the terahertz wave spectrometer 1 according to the fourth embodiment of the present invention. The same or equivalent portions as those in the terahertz wave spectrometer 1 of the first embodiment are indicated by the same reference numerals, and description of these portions are omitted.

The present embodiment employs the excitation-light optical system 30 in the same manner as the first embodiment. The present embodiment employs the optical switching device 10*a* as the terahertz wave generator 10 in the same manner as the first embodiment.

However, according to the present embodiment, the single optical switching device 20*a* is not used as the terahertz wave detector 20, but a CCD device 20*c* of an optical-switch two-dimensional arranged type is used as the terahertz wave detector 20. The CCD device 20*c* is a two-dimensional detector. A plurality of optical switching devices 20*a* are arranged two-dimensionally on the optical-switch two-dimensional arranged type CCD device 20*c*.

In the terahertz wave optical system 38, the terahertz wave is guided by the off-axis paraboloidal mirror 13 so as to be irradiated as a collimated light on the sample B and to pass through the sample B. According to the present embodiment, the terahertz wave, having passed through the sample B, is not collected or focused, but falls incident on the optical-switch two-dimensional arranged type CCD device 20*c* substantially in the collimated state. In the probe-light optical system 35, the probe light is adjusted in its timing by the variable optical delay device 40, and thereafter reflected by the reflective mirror 33, magnified by a lens 25, and converted by another lens 26 into a substantially-parallel, collimated beam. The probe light then falls incident on the optical-switch two-dimensional arranged type CCD device 20*c* in the collimated, substantially-parallel state. With this construction, each optical switching device 20*a* provided on the optical-switch two-dimensional arranged type CCD device 20*c* can detect the terahertz wave that falls incident on the corresponding position.

Figure 12A:
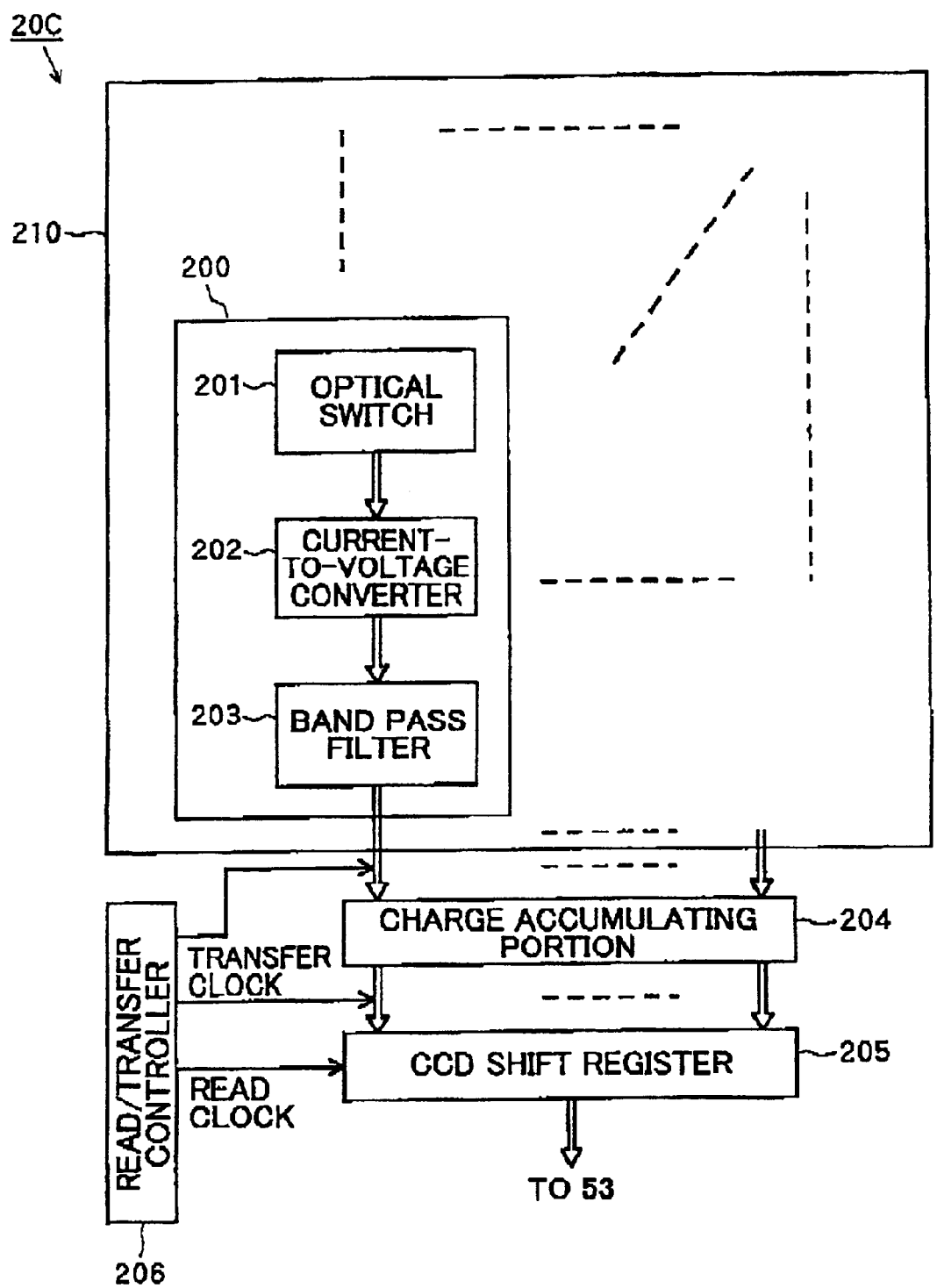
FIG. 12(A) is a block diagram showing the structure of a CCD device of an optical switch two-dimensional arranging type, provided in the terahertz wave spectrometer of FIG. 11, for terahertz wave detection.

For example, as shown in FIG. 12(A), the optical-switch two-dimensional arranged type CCD device 20*c* has: a terahertz wave detection portion 210, a charge accumulating portion 204, a CCD shift register 205, and a reading/transfer control portion 206. The terahertz wave detection portion 210 has a plurality of units 200, which are arranged two-dimensionally. The charge accumulating portion 204 is for accumulating signals from the plurality of units 200 in the terahertz wave detection portion 210. The CCD shift register 205 is for reading charges from the charge accumulating portion 204. The reading/transfer control portion 206 is for controlling transfer and reading of charges.

Each of the plurality of units 200, which constitute the terahertz wave detection portion 210, is constructed from: an optical switch 201, a current-to-voltage converting circuit 202, and a band-pass filter 203. The optical switch 201 has the structure the same as that of the optical switching device 20a shown in FIG. 2(B). The current-to-voltage converting circuit 202 and the band-pass filter 203 have the same structure as the current-to-voltage converting amplifier 51 and the band-pass filter 54 in the second embodiment shown in FIG. 8(A). In other words, the unit 200, per se. performs a part of the function of the spectroscopic processor 50 which performs the frequency analyzing operation.

Figure 12B:
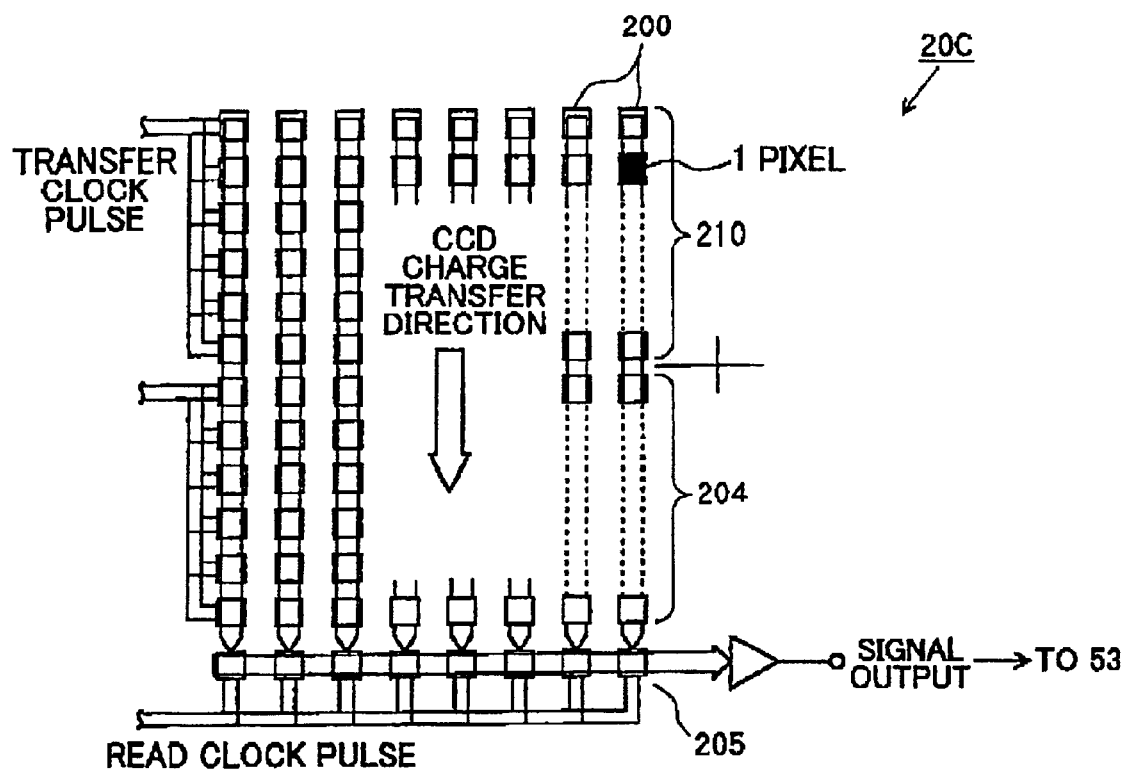
FIG. 12(B) shows a circuit structure of one example of the CCD device of the optical switch two-dimensional arranging type of FIG. 12(A)

In the terahertz wave detecting portion 210, the plurality of units 200 are arranged two-dimensionally as shown in FIG. 12(B). Each unit 200 corresponds to one pixel. All the units 210 constitute one screen. The plural units 200 are connected to the charge accumulating portion 204. The charge accumulating portion 204 is constructed from a plurality of capacitors (condensers), the number of which is equal to the number of the units 200. The charge accumulating portion 204 can accumulates one screen's worth of signal charges transmitted from all the units 200. The charge accumulating portion 204 is connected to the CCD shift register 205. The CCD shift register 205 is for transferring the one screen's worth of signal charges that are accumulated in the charge accumulating portion 204. The reading/transfer control portion 206 is for controlling transfer and reading of charges, by outputting transfer clock pulses and read clock pulses. The transfer clock pulses are signals used for controlling transfer of charges from each unit 200 to the charge accumulating portion 204 and transfer of charges at the charge accumulating portion 204. The read clock pulses are signals used for controlling reading of charges from the charge accumulating portion 204 by the CCD shift register 205.

With the above-described structure, the two-dimensional image of the terahertz wave falls incident on the optical-switch two-dimensional arranged type CCD device 20c. In each unit 200, the two-dimensional image is detected as a pixel signal by the optical switch 201, subjected to current-to-voltage conversion by the current-to-voltage conversion circuit 202, and subjected to frequency selection by the band-pass filter 203. The two-dimensional image is then transferred by the CCD shift register 210 through the charge accumulating portion 204, and is outputted, as a two-dimensional charge image, to the analyzing device 53 in the spectroscopic processor 50. The thus obtained two-dimensional charge image corresponds to the two-dimensional image information of the sample B, through which the terahertz wave has been transmitted.

As described above, according to the present embodiment, it is possible to perform a two-dimensional imaging with the terahertz wave all at once without moving the sample B by any moving device or the like. The components shown in FIGS. 12(A)–12(B) are relatively simplified, and therefore can be easily constructed as an integrated circuit. It is therefore possible to make up the architecture of the terahertz wave spectroscopic imaging system less costly.

It is possible to perform a measurement of a one-dimensional imaging by replacing the optical-switch two-dimensional arranged type CCD device 20c with a one-dimensional detector.

In the above-described first through fourth embodiments, the optical switching devices 10a and 20a are used as the terahertz wave generator 10 and the terahertz wave detector 20. However, it is possible to employ terahertz wave generators and terahertz wave detectors having other various constructions. For example, it is possible to employ electro-optic crystals (EO crystals) as the terahertz wave generator 10 and the terahertz wave detector 20.

Fifth Embodiment

Next, a terahertz wave spectrometer according to a fifth embodiment of the present invention will be described with reference to FIG. 13.

Figure 13:
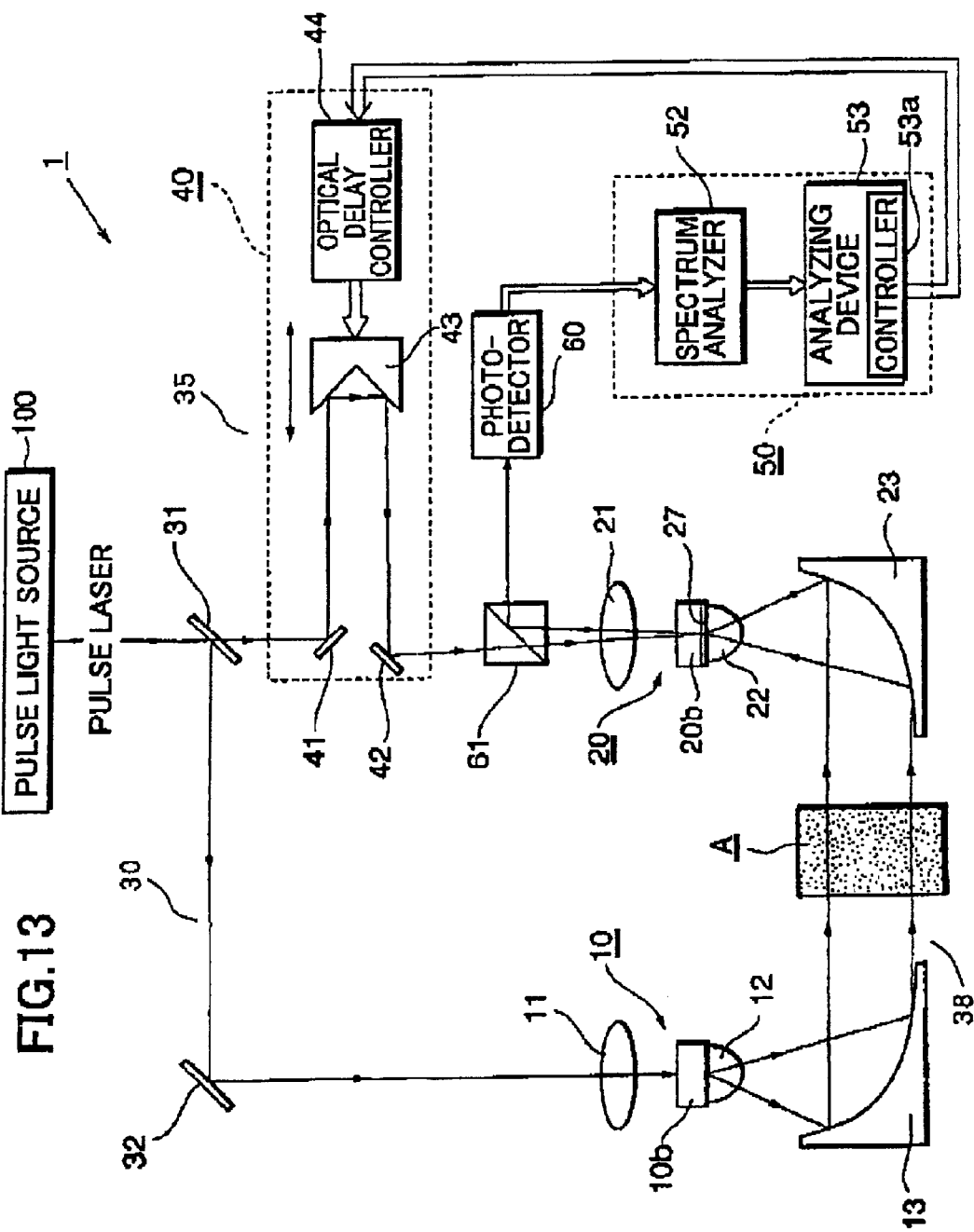
FIG. 13 is a schematic diagram showing the structure of a terahertz wave spectrometer according to a fifth embodiment of the present invention.

FIG. 13 shows the structure of the terahertz wave spectrometer 1 according to the fifth embodiment of the present invention. The same or equivalent portions as those in the terahertz wave spectrometer 1 of the first embodiment are indicated by the same reference numerals, and description of these portions are omitted.

In the present embodiment, an electro-optic crystal 10b is used as the terahertz wave generator 10, and another electro-optic crystal 20b is used as the terahertz wave detector 20.

Because the electro-optic crystal lab is used as the terahertz wave generator 10, when an excitation light, such as a femtosecond optical pulse, from the pulse light source 100 falls incident on the electro-optic crystal 10b, the electro-optic crystal 10b generates a terahertz wave according to an optical rectification function by an inverse Pockels effect.

Because the electro-optic crystal 20b is used as the terahertz wave detector 20, the electro-optic crystal 20b generates the Pockels effect due to the electric field of the incident terahertz wave. As a result, birefringence changes in the electro-optic crystal 20b. The probe light having a predetermined polarization state is caused to pass through the electro-optic crystal 20b. By detecting the change in the intensity of the probe light that has passed through the electro-optic crystal 20b, it is possible to detect the terahertz wave that falls incident on the electro-optic crystal 20b.

Because the electro-optic crystal 20b is used in this way, it is possible to generate and detect terahertz wave with a higher frequency (shorter wavelength) than the case where the optical switching device is used.

According to the present embodiment, the excitation light from the pulse light source 100 falls incident on the electro-optic crystal 10b via the objective lens 11. The electro-optic crystal 10b constitutes the terahertz wave generator 10. As a result, the optical-rectification occurs in the electro-optic crystal 10b due to the inverse Pockels effect, whereupon terahertz wave, to be used for the spectroscopic operation, is generated. The thus generated terahertz wave is guided by the output lens 12 and the off-axis paraboloidal mirror 13 to fall incident on the sample A as a collimated light. The terahertz wave passes through the sample A, and is guided by the off-axis paraboloidal mirror 23 and the input lens 22 to fall incident on the electro-optic crystal 20b, which constitutes the terahertz wave detector 20.

A dielectric multi-layered mirror 27 is provided on the surface of the electro-optic crystal 20b on its input lens 22 side (terahertz wave input side). The dielectric multi-layered mirror 27 is formed by deposition. The dielectric multi-layered mirror 27 is capable of reflecting off the probe light. The variable optical delay device 40 periodically changes or vibrates the timing when the probe light falls incident on the electro-optic crystal 20b. A polarization beam splitter 61 converts the probe light into a linearly-polarized light. The probe light from the polarization beam splitter 61 falls incident on the electro-optic crystal 20b via the objective lens 21. If the terahertz wave falls incident on the electro-optic crystal 20b when the probe light falls incident on the electro-optic crystal 20b, the Pockels effect occurs in the electro-optic crystal 20b due to the electric field of the terahertz wave, and birefringence is changed accordingly.

The probe light passes through the electro-optic crystal 20b, reflects off the dielectric multi-layered mirror 27, again passes through the electro-optic crystal 20b, and finally outputs from the electro-optic crystal 20b. By thus passing through the electro-optic crystal 20b where the birefringence is changed, the polarization state of the probe light changes. The probe light, whose polarization state is thus changed, falls incident on the polarization beam splitter 61. A linearly-polarized component of the probe light, whose polarization direction is perpendicular to the polarization direction of the original polarization state of the probe light, reflects off the polarization beam splitter 61 in a predetermined direction, thereby outputting from the polarization beam splitter 61. A photodetector 60, such as a photo-diode or the like, detects and measures the amount of the light, thus outputted from the polarization beam splitter 61, by converting the light amount into an electric voltage or an electric current. It is therefore possible to detect the terahertz wave falling incident on the electro-optic crystal 20b.

The photodetector 60 is connected to the spectrum analyzer 52 and the analyzing device 53 in the spectroscopic processor 50. The frequency analyzing operation and the spectroscopic analyzing operation are conducted in the same manner as in the case where the optical switching device 20a is used as the terahertz wave detector 20. It is possible to use one or more band-pass filter(s) 54 in the same manner as in the second and third embodiments, instead of using the spectrum analyzer 52. In a modification, the terahertz wave generator 10 may be constructed from the optical switching device 10a, while the terahertz wave detector 20 is constructed from the electro-optic crystal 20b. Alternatively, the terahertz wave generator 10 may be constructed from the electro-optic crystal 10b, while the terahertz wave detector 20 is constructed from the optical switching device 20a.

When the electro-optic crystal is thus used for generating and detecting the terahertz wave, it is preferable to locate the electro-optic crystal in an orientation that satisfies a predetermined relationship between the polarization direction of the excitation light, of the probe light, and of the terahertz wave. Optical elements such as a wave plate, a polarizer, and a Babinet-Soleil compensator may be optionally located in the excitation light optical system 30, the probe light optical system 35, and the optical path from the light source 100 to the beam splitter 31 where the optical light from the light source 100 is separated into the excitation light and the probe light. Those optical elements can adjust the polarization state of the optical pulse.

Various electro-optic crystals such as ZnTe, GaP, and DAST can be used as the electro-optic crystal.

Sixth Embodiment

Next, a terahertz wave spectrometer according to a sixth embodiment of the present invention will be described with reference to FIG. 14.

Figure 14:
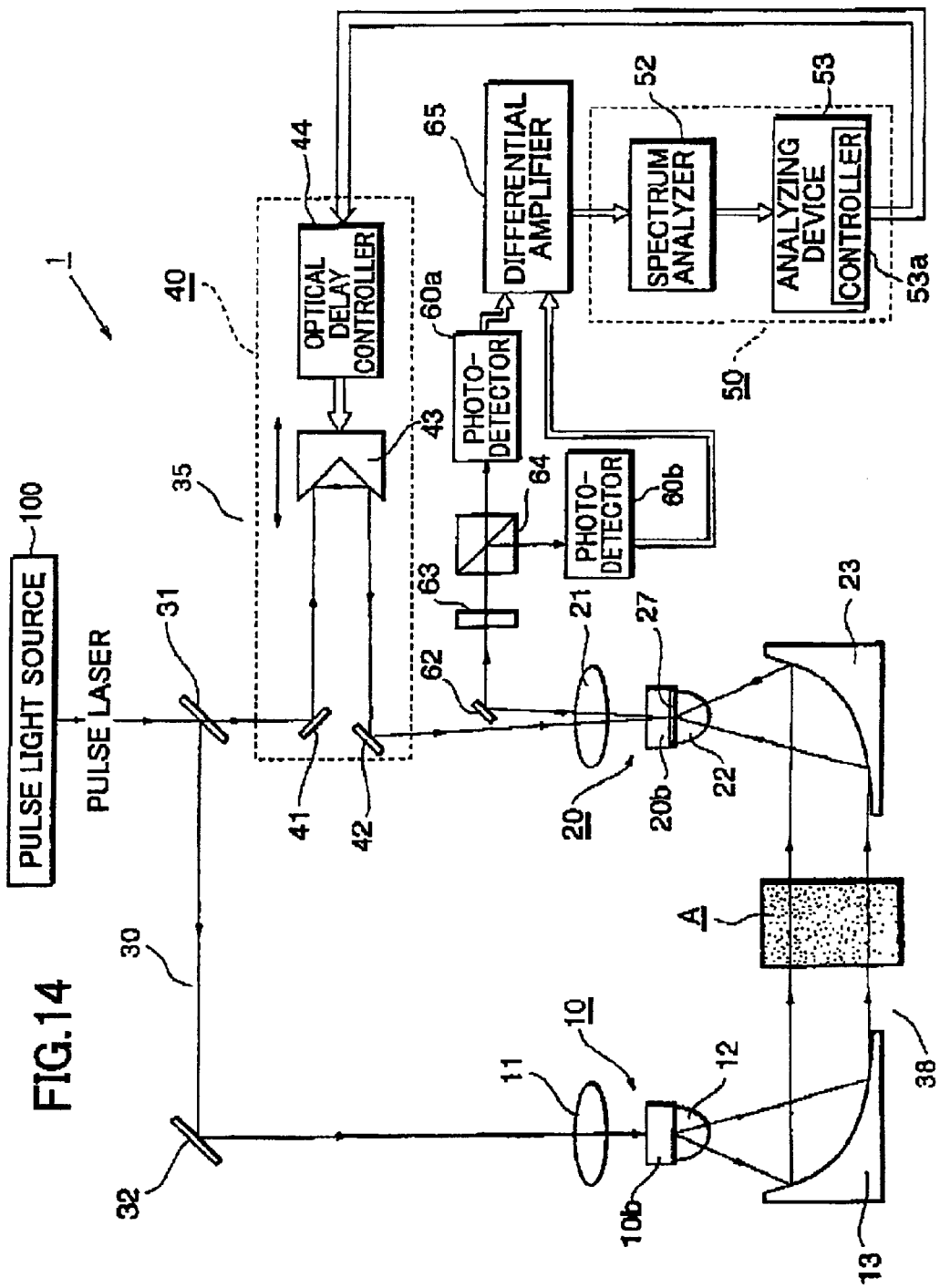
FIG. 14 is a schematic diagram showing the structure of a terahertz wave spectrometer according to a sixth embodiment of the present invention.

FIG. 14 shows the structure of the terahertz wave spectrometer 1 according to the sixth embodiment of the present invention. The same or equivalent portions as those in the terahertz wave spectrometer 1 of the fifth embodiment are indicated by the same reference numerals, and description of these portions are omitted.

The present embodiment employs the terahertz wave generator 10, the terahertz wave detector 20, the optical systems 30, 35, and 38, and the spectroscopic processor 50 in the same manner as the fifth embodiment. However, the present embodiment differs from the fifth embodiment in the manner how to detect the probe light that has passed through the electro-optic crystal 20b that constitutes the terahertz wave detector 20.

According to the present embodiment, the direction of the traveling path of the probe light, which has passed through the electro-optic crystal 20b and which has reflected off the dielectric multi-layered mirror 27, is changed by a reflection mirror 62 into a predetermined direction. It is noted that it is possible to employ a beam splitter or the like, instead of using the reflection mirror 62. The probe light passes through a predetermined wave plate 63, thereby being converted into a predetermined polarization state. The probe light is then split by a polarization beam splitter 64 into two probe light components, whose amounts are then detected and measured by photodetectors 60a and 60b, respectively.

The polarization state of the probe light changes when the terahertz wave falls incident on the electro-optic crystal 20b. As a result, the correlation, between the probe light components, which are separated from each other by the polarization beam splitter 64, changes. The correlation is, for example, a ratio of the amounts of the probe light components. It is therefore possible to detect the terahertz wave and to measure the intensity of the terahertz wave, by measuring the correlation between the detection signals outputted from the two photodetectors 60a and 60b, and by measuring the change in the correlation.

According to the present embodiment, a differential amplifier 65 is connected to the photodetectors 60a and 60b, in order to accomplish the above-described measurement operation. In this way, according to the present embodiment, the electro-optic crystal is used, and the terahertz wave is detected by measuring the difference, between the amounts of the probe light components, which are separated from each other by the polarization beam splitter 64, and by measuring the change in the difference. By thus obtaining a difference between the measured data values, it is possible to cancel out the effects from the intensity noise of the laser 100 that serves as the light source of the probe light. It is therefore possible to enhance the accuracy and the signal-to-noise ratio of the measurement. The differential amplifier 65 is connected to the spectrum analyzer 52 and the analyzing device 53 in the spectroscopic processor 50. Thus, the frequency analyzing operation and the spectroscopic analyzing operation is performed in the same manner as in the other embodiments.

Seventh Embodiment

Next, a terahertz wave spectrometer according to a seventh embodiment of the present invention will be described with reference to FIGS. 15(A) and 15(B).

Figure 15A:
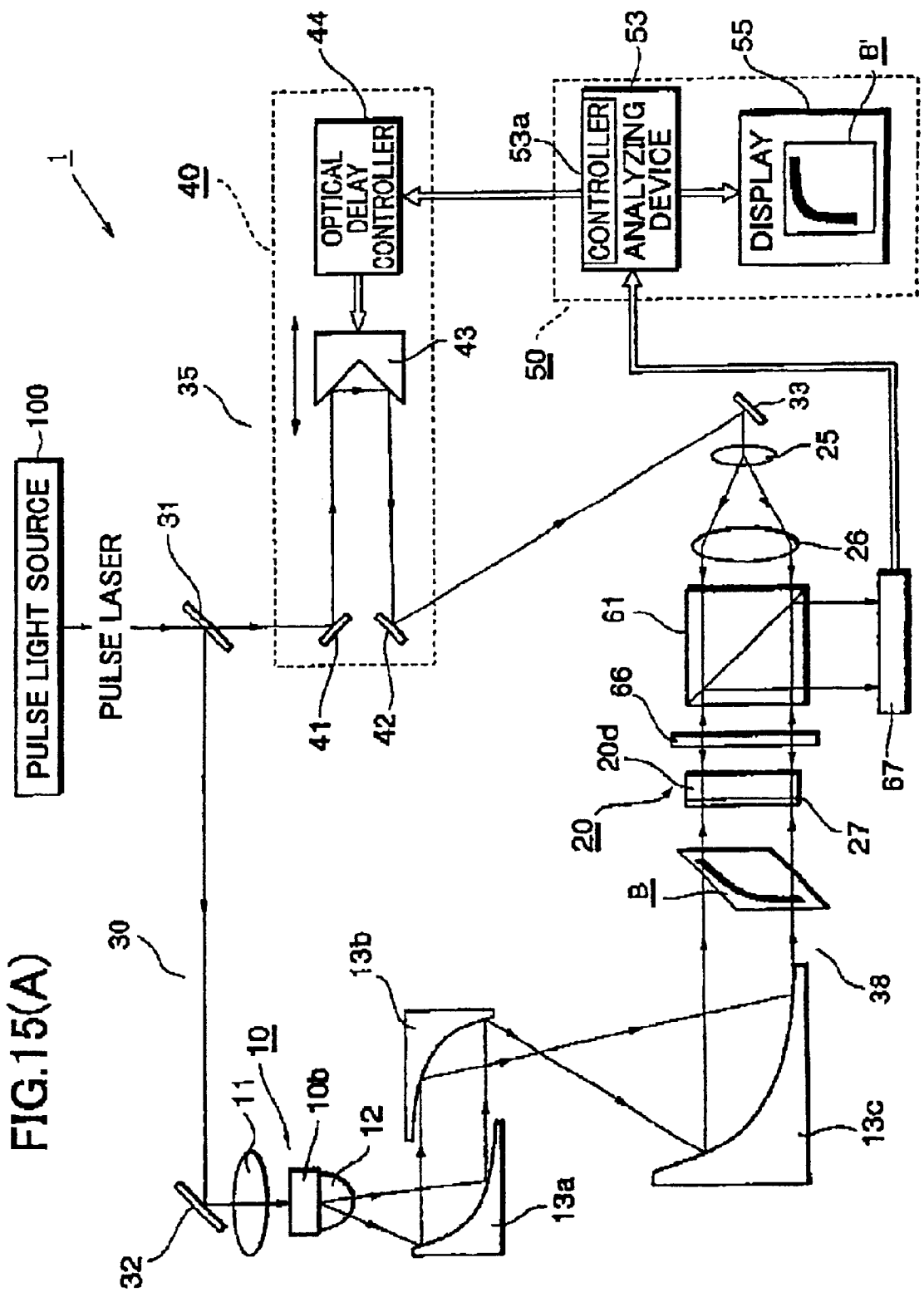
FIG. 15(A) is a schematic diagram showing the structure of a terahertz wave spectrometer according to a seventh embodiment of the present invention.

FIG. 15(A) shows the structure of the terahertz wave spectrometer 1 according to the seventh embodiment of the present invention. The same or equivalent portions as those in the terahertz wave spectrometer 1 of the fifth embodiment are indicated by the same reference numerals, and description of these portions are omitted.

The present embodiment employs the excitation optical system 30 in the same manner as the fifth embodiment. The present embodiment employs the electro-optic (EO) crystal 10b as the terahertz wave generator 10. However, the present embodiment employs, as the terahertz wave detector 20, an electro-optic (EO) crystal 20d for two-dimensional detection. The electro-optic crystal 20d has a predetermined size that corresponds to the size of the sample B, thereby enabling a two-dimensional imaging.

The terahertz wave generated from the EO crystal 10b that constitutes the terahertz wave generator 10 is magnified by off-axis paraboloidal mirrors 13a and 13b in the terahertz wave optical path 38, and then converted by another off-axis paraboloidal mirror 13c into substantially a parallel, collimated light, before being irradiated onto the sample B and passing through the sample B. The terahertz wave having passed through the sample B is not collected or focused, but maintains its collimated state, and falls incident on the EO crystal 20d, which constitutes the terahertz wave detector 20 and which can perform a two dimensional detection. On the other hand, the probe light reflects off the reflection mirror 33 in the probe light optical path 35, is magnified by the lens 25, and then is converted by the lens 26 into substantially a parallel, collimated light. Then, the probe light is converted into a predetermined polarization state by the polarization beam splitter 61 and the wave plate 66, before being irradiated onto the EO crystal 20d.

The probe light reflects off the dielectric multi-layered mirror 27, which is formed on the EO crystal 20d, and again passes through the wave plate 66. Then, in the same manner as in the fifth embodiment shown in FIG. 13, some component of the probe light reflects off the polarization beam splitter 61 to output therefrom. The light amount of the probe light component, outputted from the polarization beam splitter 61, is detected and measured as a two-dimensional image by a CCD device 67 of a photodetector two-dimensional arranged type, thereby achieving the terahertz wave two-dimensional imaging operation.

Figure 15B:
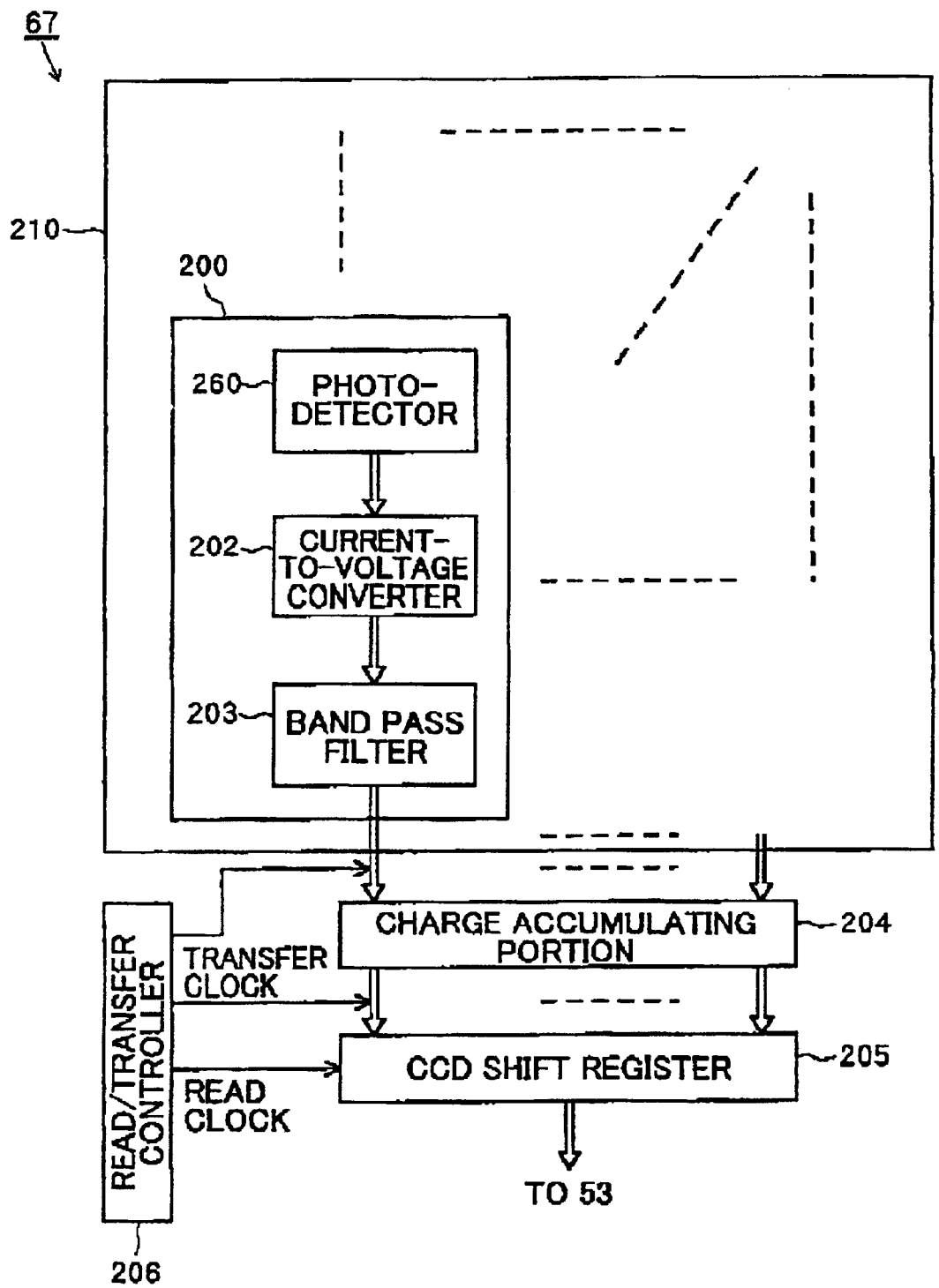
FIG. 15(B) is a block diagram showing the structure of a CCD device of a photodetector two-dimensional arranging type, provided in the terahertz wave spectrometer of FIG. 15(A)

As shown in FIG. 15(B), the CCD device 67 of the photodetector two-dimensional arranged type has substantially the same structure as the CCD device 20c of the optical-switch two-dimensional arranged type which is employed in the fourth embodiment. The CCD device 67 is, however, different from the CCD device 20c in that the CCD device 67 employs photodetectors 260 instead of using the optical switches 201. Each photodetector 260 has the same structure with the photodetector 60 employed in the fifth embodiment (FIG. 13). More specifically, in the CCD device 67, a unit corresponding to each pixel is constructed from: the photodetector 260, the current-to-voltage conversion circuit 202 for converting an electric detection current from the photodetector 260 into an electric voltage, and the band-pass filter 203 for selecting a predetermined frequency signal from the voltage signal from the current-to-voltage conversion circuit 202. The plurality of units 200, each having the above-described structure, are arranged two-dimensionally, similarly to the CCD device 20c shown in FIG. 12(B), and are connected to the analyzing device 53 via the charge accumulating portion 204 and the CCD shift register 205.

It is preferable to use, as the wave plate 66, a one-eight retardation plate, in order to give a total phase difference of a quarter wavelength, for example, onto the probe light when the probe light travels forward and backward. It may be possible to optionally change the setting of the wave plate or the like in association with the polarization state of the probe light, the orientation of the EO crystal, and the like.

The above description of the present embodiment is directed to the terahertz wave imaging, wherein the EO crystal, which has a large area corresponding to the size of the sample, is used to obtain a two-dimensional image at once. However, the EO crystal can be applied to another type of two-dimensional imaging, wherein the terahertz wave is focused and irradiated onto a single position of the sample, while moving the sample two-dimensionally, thereby scanning the sample in the similar manner as in the embodiment of FIG. 10 where the optical switches are used.

Eighth Embodiment

Next, a terahertz wave spectrometer according to an eighth embodiment of the present invention will be described with reference to FIGS. 16 and 17.

Figure 16:
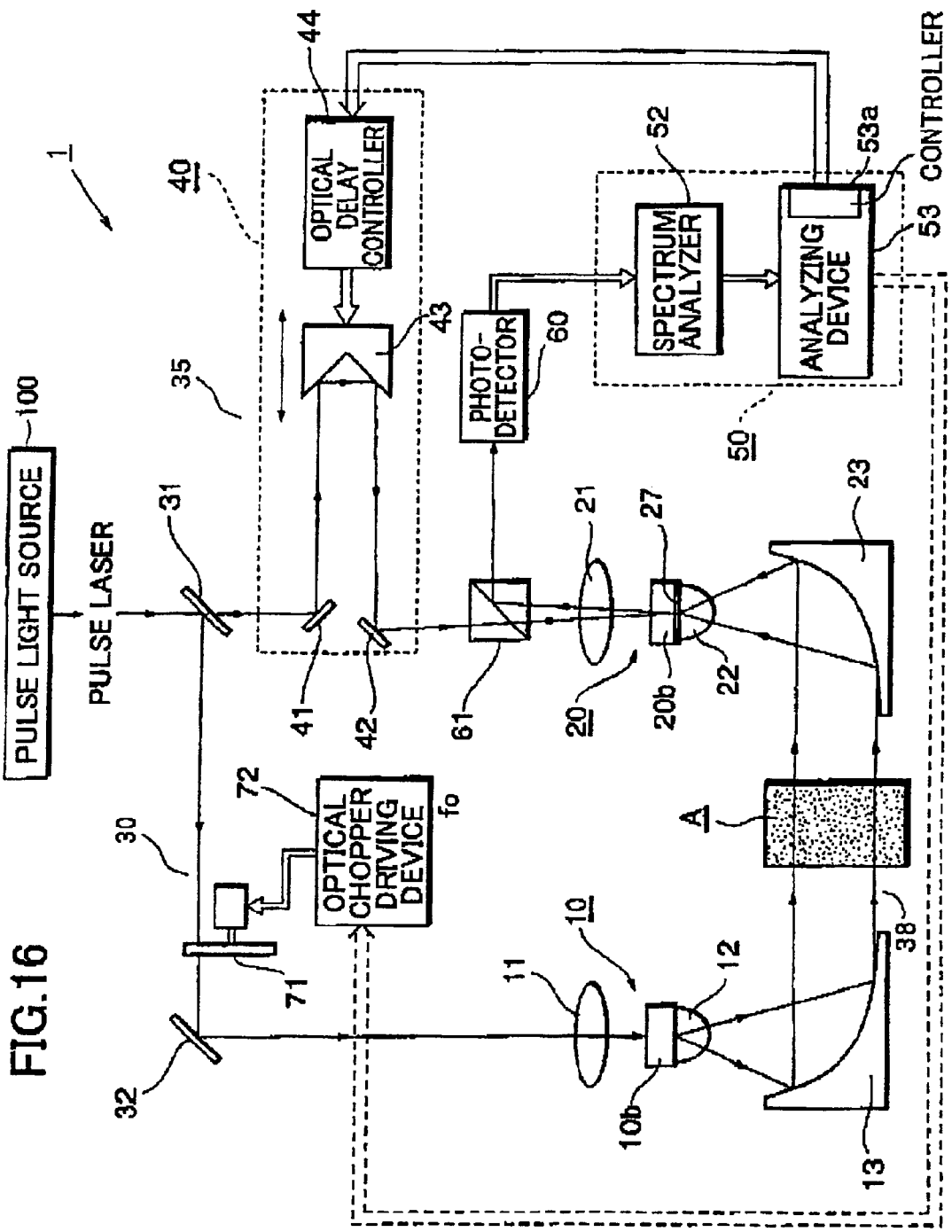
FIG. 16 is a schematic diagram showing the structure of a terahertz wave spectrometer according to an eighth embodiment of the present invention.
Figure 17:
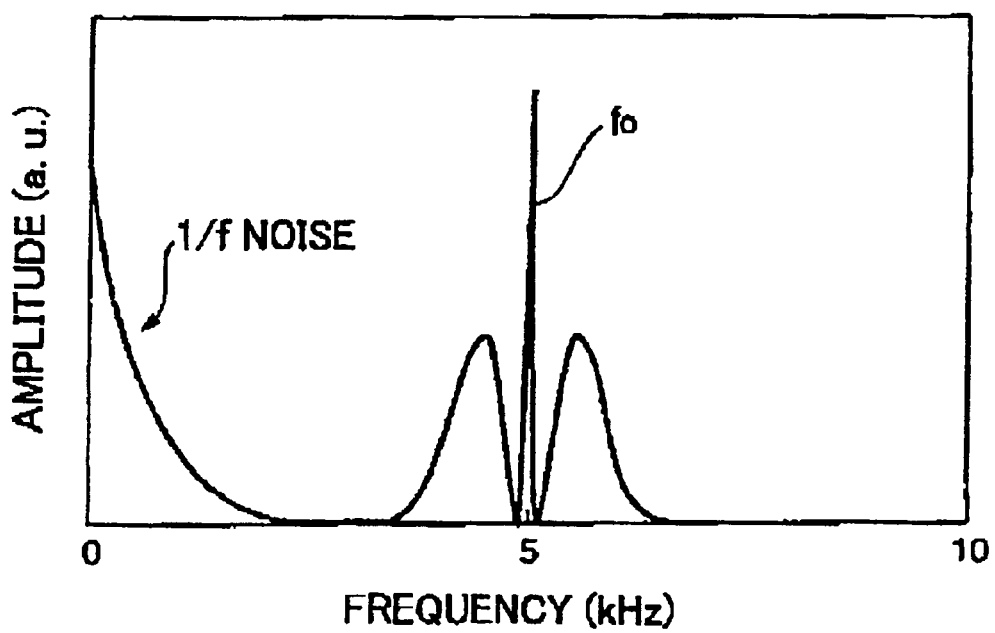
FIG. 17 is a graph showing a frequency amplitude spectrum obtained by the terahertz wave spectrometer of FIG. 16.

FIG. 16 shows the structure of the terahertz wave spectrometer 1 according to the eighth embodiment of the present invention. The same or equivalent portions as those in the terahertz wave spectrometer 1 of the fifth embodiment are indicated by the same reference numerals, and description of these portions are omitted.

The present embodiment employs the terahertz wave generator 10, the terahertz wave detector 20, the probe light optical system 35, the terahertz wave optical system 38, the photodetector 60, and the spectroscopic processor 50 in the same manner as the fifth embodiment. However, the present embodiment differs from the fifth embodiment in that an optical chopper 71 is additionally mounted in the excitation light optical system 30 at a predetermined position relative to the optical path of the excitation light.

Some terahertz wave spectroscopic measurement will possibly suffer from noise or noise light generated in the femto-second pulse laser (light source 100 for the excitation light and the probe light). It is especially noted that a large noise, called "1/f noise", exists in the low frequency region. Such noise degrades the signal-to-noise ratio of the measurement when the variable optical delay device 40 performs vibration at a frequency of 1 kHz or less.

In order to solve this problem, the optical chopper 71 is mounted in the excitation light optical system 30 as shown in FIG. 16 in order to further modulate and control the on and off operations of the excitation light. The ON/OFF operation by the optical chopper 71 is driven and controlled by an optical chopper driving device 72. For example, the excitation light is turned ON and OFF by the optical chopper 71 at a fixed frequency. It is assumed that a spectroscopic measurement is attained in a manner that the optical chopper driving device 72 drives the optical chopper 71 by the frequency f0=5 kHz and the variable optical delay device 40 performs vibration at the frequency fs=100 Hz. In such a case, a frequency spectrum shown in FIG. 17 is obtained based on the frequency analysis of a detection signal.

The frequency spectrum has, as the center frequency thereof, the driving frequency f0=5 kHz of the optical chopper 71, and has a pair of sidebands on both sides of the center (the driving frequency f0=5 kHz) in symmetric relation. Each side band is the terahertz wave frequency spectrum that corresponds to the frequency spectrum of FIG. 7. This method is analogous to the frequency modulation scheme employed for an FM radio. In this case, it is possible to prevent the spectroscopic measurement from suffering from the 1/f noise, which occurs in the low frequency range as shown in the graph of FIG. 17, by using the spectrum analyzer 52, for example, to measure the frequency range of 5 kHz to 7 kHz to obtain the terahertz wave frequency spectrum. It is therefore possible to enhance the signal-to-noise ratio. The structure of the present embodiment can be modified by connecting the optical chopper driving device 72 to the analyzing device 53 as indicated by broken lines in FIG. 16. The analyzing device 53 can control the driving frequency, or the like, of the optical chopper driving device 72.

The terahertz wave spectrometer of the present invention is not limited to the above-described embodiments, but can be modified in a variety of ways.

For example, the present invention is not limited to the methods in which the optical switching device or the EO crystal is used for generating or detecting terahertz wave, but also to other methods wherein terahertz wave is generated and detected by using a quantum well structure, electrooptic Cerenkov radiation, coherent phonon, or the like.

Regarding the structure of the spectroscopy measurement, the above description is directed to the structure that performs measurement to detect the characteristic how terahertz wave is transmitted through the samples A and B. However, other various types of structure can be employed that allows the sample to affect the terahertz wave. For example, it is possible to employ such a structure that measures how the sample reflects the terahertz wave.

Figure 18:
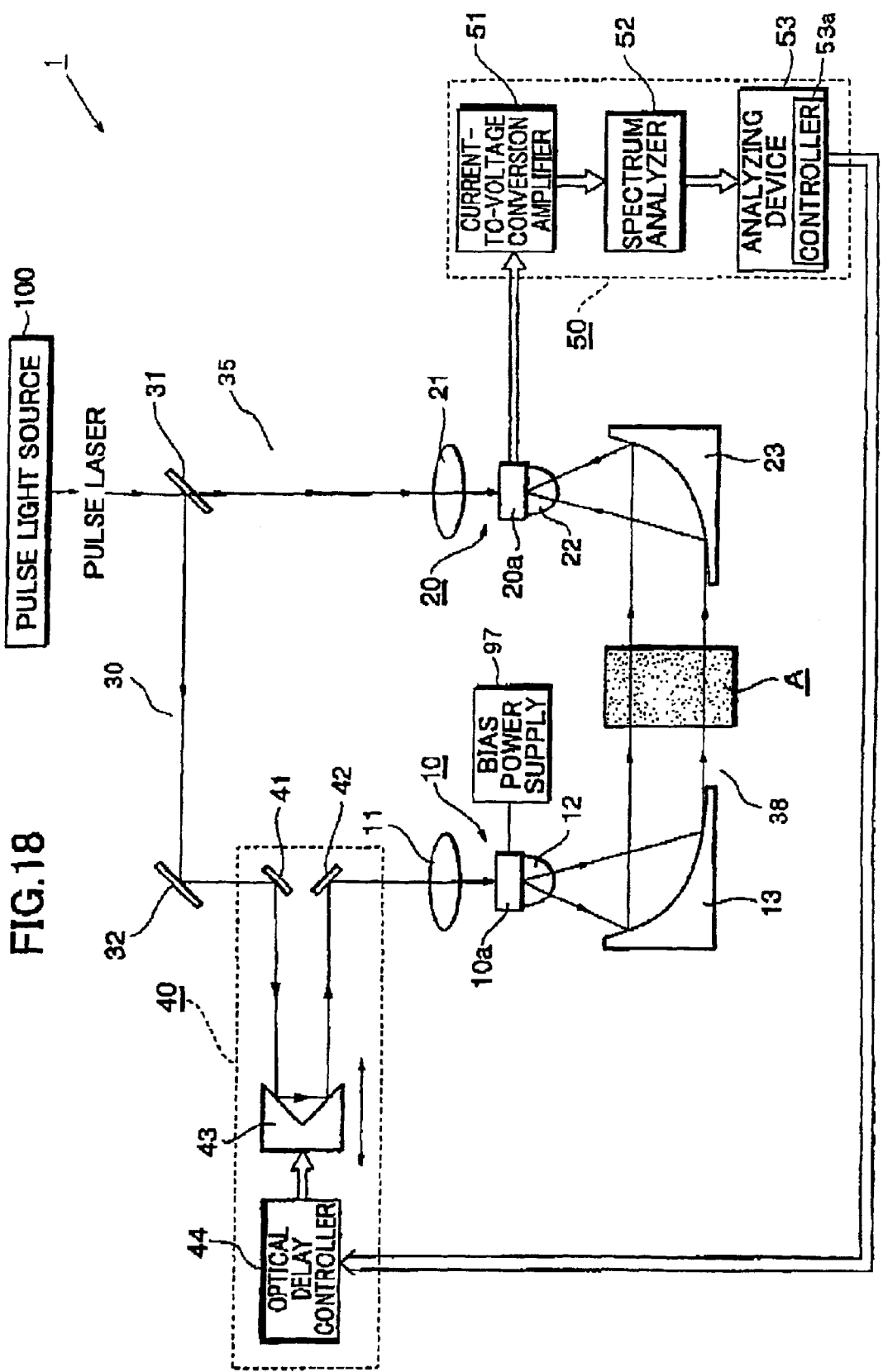
FIG. 18 is a schematic diagram showing the structure of a modification of the terahertz wave spectrometer of FIG. 1.

In all the embodiments described above, the variable optical delay device 40 is mounted in the probe light optical system 35. However, the variable optical delay device 40 may be mounted in the excitation light optical system 30 as shown in FIG. 18. In this case, it is possible to vibratingly vary, relative to the terahertz wave detection timings, the timings when terahertz wave is generated by irradiation of the excitation light on the terahertz wave generator 10. Also in this case, the scale conversion can be attained in the same way as in the embodiments. The measurement can be attained by the frequency analyzing device in the same way as in the embodiments.

The variable optical delay device 40 can perform vibration operation in various waveforms, other than the triangular wave, such as the trapezoidal wave, sinusoidal wave, and sawtooth wave as shown in FIGS. 5(B), 5(C), and 5(D). In the case where the sinusoidal wave is used, for example, the positional vibration will not have a linear correspondence with time. The frequency spectrum of the detection signal will not have exactly the same shape with that of the terahertz wave, but will have a similar or quasi-same shape with that of the terahertz wave. In such a case, it may be possible to correct the temporary waveform of the detection signal by using a sinusoidal wave to attain the linear correspondence between the detection signal and the terahertz wave. Alternatively, it is possible to perform the vibration in such an amplitude that is sufficiently large relative to the full scale of the time length desired to be measured. In this case, the region around the center of the vibration can be regarded as a region where the change is performed substantially linearly. Only this center-around region is used for the measurement.

The vibration frequency can be optionally set in association with the concrete structure of the variable optical delay device and with the frequency ranges measurable by the spectrum analyzer or the band-pass filter. The vibration frequency may be set in the range of about 10 Hz to 100 kHz, for example.

In the above-described embodiments, the movable reflector 43, in the variable optical delay device 40, is constructed from an audio speaker 43b, as shown in FIG. 4, to vibrate the probe light irradiation timing at the predetermined frequency. The audio speaker can perform vibration at a frequency of about 20 Hz to 20 kHz, for example, that is a human audio frequency range. By constructing the movable reflector 43 from a small-weight retroreflector, for example, the movable reflector 43 can be driven at a frequency of about several kHz. However, the movable reflector 43 may be constructed from any devices other than the retroreflector.

The movable reflector 43 may be constructed from any devices other than the speaker. FIGS. 19–22 show examples of the structure of the movable reflector 43 other than the example of the speaker.

Figure 19:
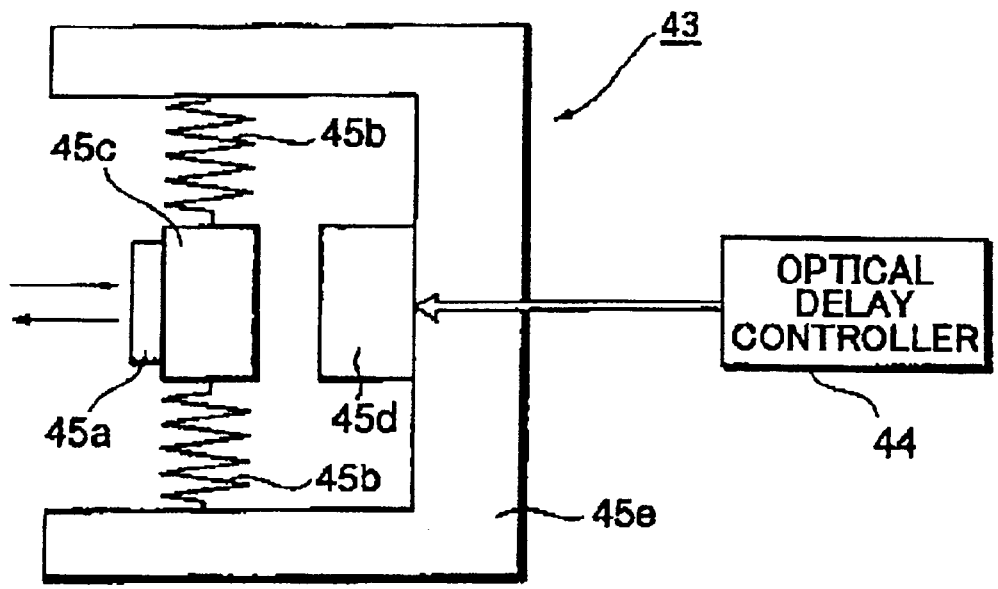
FIG. 19 shows the structure of another example of a movable reflector in the variable optical delay device.

FIG. 19 shows the structure of the movable reflector 43 that uses a magnet. In this example, an optical reflecting portion 45a is fixed to a magnet 45c, which is attached via springs 45b to a support stand 45e. An electromagnet 45d is fixed to the support stand 45e at a position opposing the magnet 45c. The reflecting portion 45a is vibrated when the electromagnet 45d is driven by a driving signal supplied from the optical delay controller 44. This construction is analogous to the structure of an audio speaker. This simple structure is capable of obtaining a quick response time, similarly to an optical pick-up for a compact disc.

It is preferable to use, as the optical reflecting portion 45a, a normal mirror rather than the retroreflector. The normal mirror has a weight smaller than the retroreflector. It is noted that the retroreflector can be advantageously used as the movable reflector because the retroreflector can reflect incident light in a direction the same as the light incident direction even when the incident light falls incident on the movable reflector in any directions. Contrarily, normal mirrors generally reflect incident light in an optical path that is different from the optical path of the incident light. It is therefore necessary to take into consideration that the optical path of the incident light should be normal to the optical reflecting portion 45a.

Figure 20:
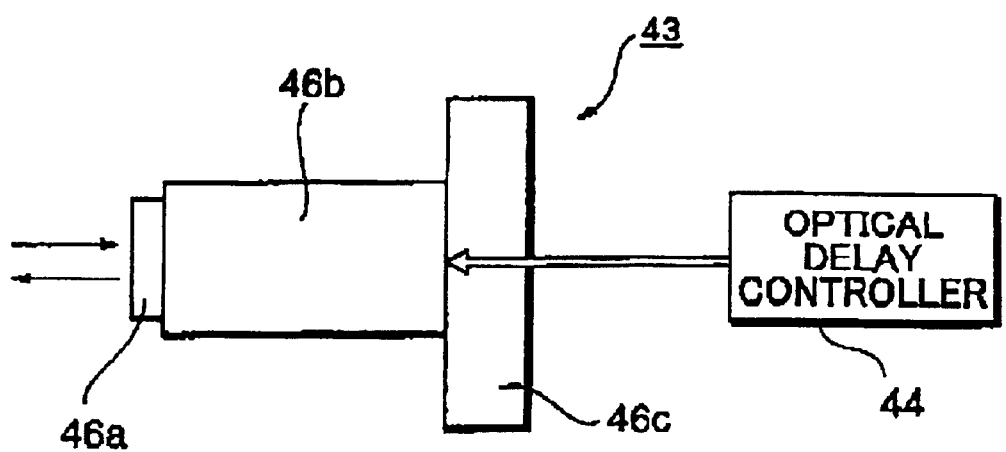
FIG. 20 shows the structure of another example of the movable reflector in the variable optical delay device.

FIG. 20 shows the structure of the movable reflector 43 that uses a piezo-electric element. In this example, an optical reflecting portion 46a, such as a mirror, is fixed to one end of a piezo-electric element 46b. The other end of the piezo-electric element 46b is fixed to a fixed portion 46c. Because the piezo-electric element 46b expands or shrinks upon application of an electric voltage thereto, the optical reflecting portion 46a vibrates in association with application of the voltage.

Figure 21:
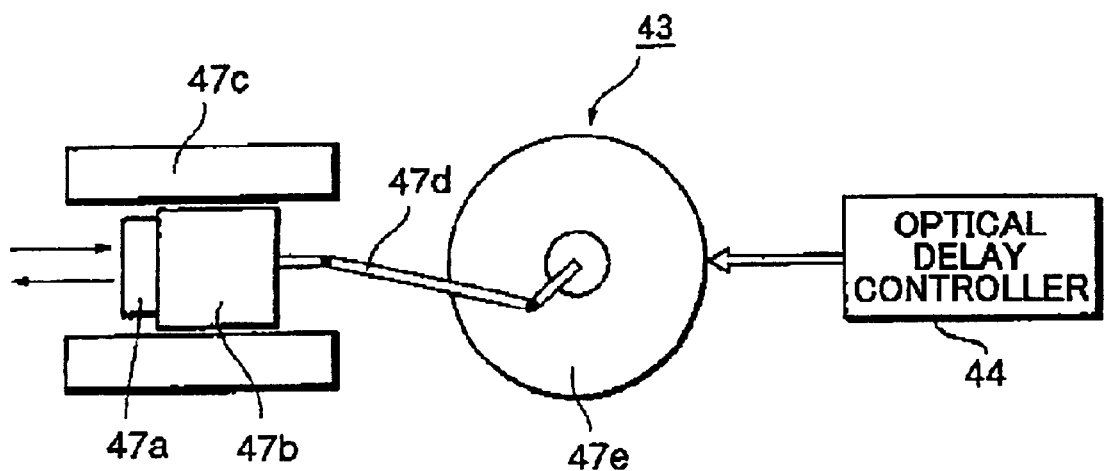
FIG. 21 shows the structure of another example of the movable reflector in the variable optical delay device.

FIG. 21 shows the structure of the movable reflector 43 that employs a piston. In the present example, an optical reflecting portion 47a, such as a mirror, is fixed to a piston 47b, which is mounted movably inside a tubular portion 47c. The piston 47b is connected to a motor 47e via a clank mechanism 47d. With this structure, the optical reflecting portion 47a vibrates in association with the rotation of the motor 47e. This structure of the movable reflector 43 employs the method of converting the rotation of the motor into the linear movement of the piston by using the clank mechanism provided to the rotational shaft of the motor. This method corresponds to the reverse operation of reciprocating engines. It is possible to attain a high speed vibration by decreasing the contact resistance between the piston 47b and the tubular portion 47c.

Figure 22:
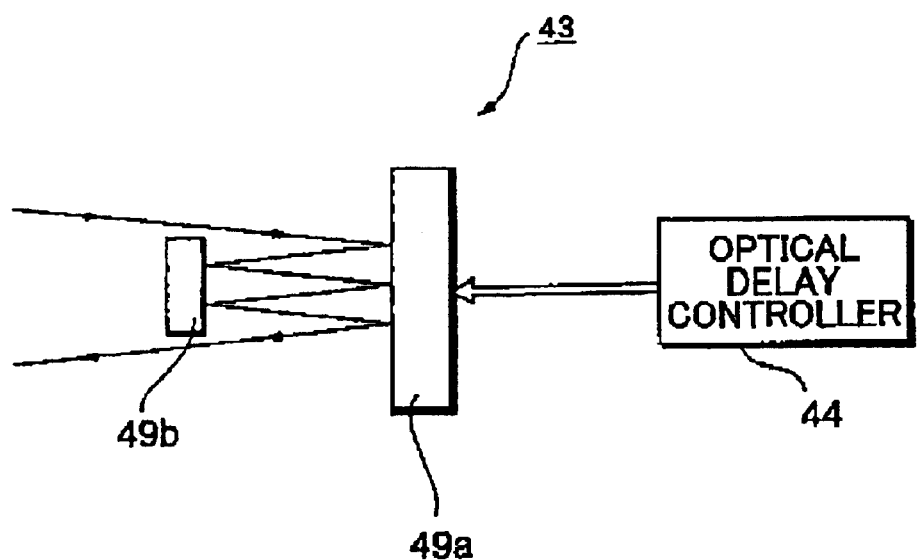
FIG. 22 shows the structure of another example of the movable reflector in the variable optical delay device.

FIG. 22 shows the structure of the movable reflector 43 that is constructed from a combination of plural mirrors. In this example, the movable reflector 43 is constructed to attain a multiple reflection by using a movable mirror 49a and a fixed mirror 49b. In this case, the probe light will travel forward and backward a plurality of times between the movable mirror 49a and the fixed mirror 49b. Accordingly, by employing the structure having the mirrors and the optical path as described above, it is possible to attain a sufficiently long delay-time difference, even if the already-described other structures of the reflection type movable reflector fail to attain the sufficiently long delay-time difference. In this example, the probe light reflects off the fixed mirror 49b twice, thereby traveling forward three times and backward three times. By moving the movable mirror 49a by an amount of 0.3 mm, for example, it is possible to change the optical path length of 1.8 mm, in total, that is six times as long as the amount of 0.3 mm.

The variable optical delay device 40 may not be constructed from the reflective mirrors 41, 42, the movable reflector 43, or the optical delay controller 44. For example, as shown in FIG. 23(A), the variable optical delay device 40 may be constructed from a movable transmitting portion 48 and the optical delay controller 44. This example is effective especially when it is impossible to mount the reflecting portion 41, 42, or 43 in the probe light optical system 35.

Figure 23B:
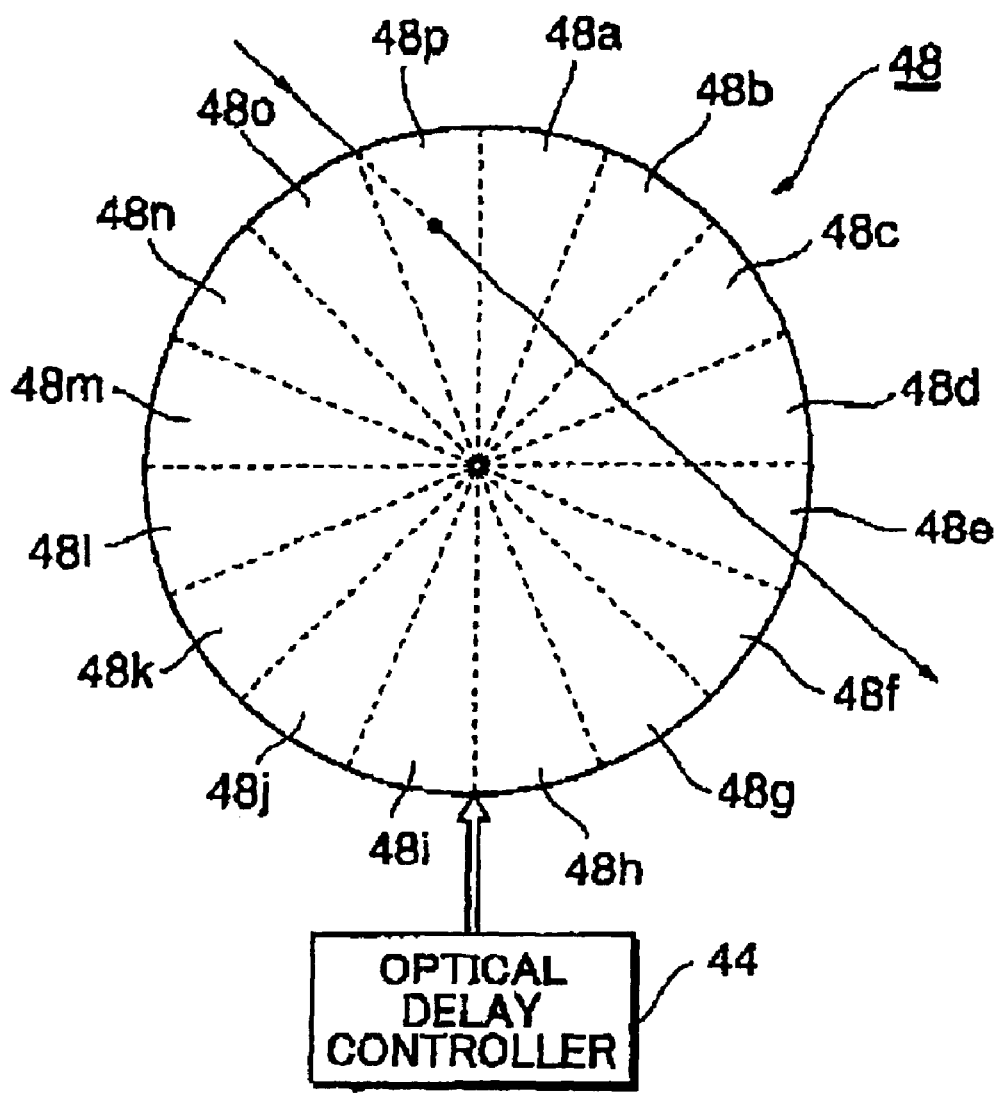
FIG. 23(B) shows the structure of one example of the movable transmitting portion of FIG. 23(A).

The movable transmitting portion 48 may be constructed from a rotational glass plate as shown in FIG. 23(B), for example. The rotational glass plate, or movable transmitting portion 48, has sixteen glass regions 48a–48p, which have glass-plate thicknesses different from one another. For example, the glass-thickness is increased step by step by a 0.3 mm pitch from the region 48a to the region 48i that opposes to the region 48a so that the region 48a has a glass-thickness of 1.0 mm, the region 48b has a glass-thickness of 1.3 mm, the region 48c has a glass-thickness of 1.6 mm, and so on. The region 48i has the maximum glass-thickness of 3.4 mm. Then, the glass-thickness is decreased step by step also by a 0.3 mm pitch from the region 48j to the region 48p so that the glass-thickness returns back to 1 mm at the region 48a. Each region 48a–48p has a uniform glass-thickness.

It is possible to vibrate the optical path length by rotating the movable transmitting portion (rotational glass plate) 48. It is noted that the index of refraction of glass is 1.5, for example. Accordingly, when the thickness of glass changes by 0.3 mm, the optical path length changes by 0.15 mm, achieving a time delay of 0.5 picoseconds. It is possible to attain a time delay difference of 4 picoseconds by using the regions 48a and 48i in the rotational glass plate of FIG. 23(B), thereby realizing the timing vibration at this time difference range.

Although the border between each two adjacent regions is discontinuous, no problem occurs actually by making the area of each region sufficiently small. It may be possible to increase the delay time difference by making large the varying pitch of the glass-thickness. It is also possible to modify the glass plate so that the optical path length increases from the region 48a to the region 48p by setting the glass-plate thickness to further increase from the region 48j to the region 48p so that the region 48j has a thickness of 3.7 mm, the region 48k has a thickness of 4.0 mm, and so on and so that the region 48p has the maximum thickness of 5.5 mm. In this case, it is possible to attain the timing vibration in the saw-tooth waveform, in which only a one-directional change is made gradual.

Alternatively, the glass plate can be modified so that the glass-thickness changes gradually continuously, for example.

The variable optical delay device 40, for varying the optical path length, may be constructed from various constructions, other than the movable reflector 43 and the movable transmitter 48. For example, it is possible to construct the variable optical delay device 40 from: an optical delay device, which is described in "Optics Commun.", vol. 36, p.406 (1981) and which uses a rotating pair of parallel mirrors that are used in an auto-collimator, for example; an optical delay device, which is described in "Optics Letters", vol 22., pp.1811–1813 (1997)) and which is constructed from a grating and a galvano mirror.

What is claimed is:

1. A terahertz wave spectrometer for performing spectroscopic measurement by using terahertz wave, comprising:
    a predetermined excitation light optical system guiding an excitation light;
    a terahertz wave generator generating terahertz wave by using the excitation light guided by the predetermined excitation light optical system;
    a terahertz wave optical system guiding the terahertz wave generated by the terahertz wave generator to a sample for spectroscopic measurement, and further guiding the terahertz wave which has been affected by the sample;
    a predetermined probe light optical system guiding a probe light that is in synchronization with the excitation light;
    a terahertz wave detector detecting, using the probe light guided by the predetermined probe light optical system, the terahertz wave that is affected by the sample and that is guided by the terahertz wave optical system, and outputting a detection signal;
    optical delay vibrating means provided in either one of the excitation light optical system and the probe light optical system, the optical delay vibrating means vibrating, at a predetermined vibration frequency, the length of the optical path of the corresponding one of the excitation light and the probe light, thereby periodically vibrating the irradiation timing of the corresponding one of the excitation light and the probe light onto a corresponding one of the terahertz wave generator and the terahertz wave detector; and
    spectroscopic processing means performing spectroscopic measurement on the sample based on the detection signal obtained by the terahertz wave detector, the spectroscopic processing means including frequency analyzing means performing frequency analysis on the detection signal that periodically changes in accordance with the vibration frequency, the frequency analyzing means performing the frequency analysis of the detection signal by performing a frequency domain measurement, the frequency-analysis result obtained by the frequency analyzing means indicating frequency-analysis information on the terahertz wave that has been affected by the sample, thereby indicating the spectroscopic information of the sample.

2. A terahertz wave spectrometer as claimed in claim 1, wherein the frequency analyzing means includes a spectrum analyzer producing a frequency spectrum by performing a frequency analysis on the detection signal.

3. A terahertz wave spectrometer as claimed in claim 1, wherein the frequency analyzing means includes a band pass filter selecting a predetermined frequency component from the detection signal.

4. A terahertz wave spectrometer as claimed in claim 3, wherein the band pass filter includes a plurality of band pass filters for selecting frequency components different from one another, the spectroscopic processing means further including correlation analyzing means determining a correlation between the plurality of frequency components selected by the plurality of band pass filters.

5. A terahertz wave spectrometer as claimed in claim 1, wherein the spectroscopic processing means further includes frequency setting/changing means controlling the optical delay vibrating means and changing or setting the value of the vibration frequency, at which the optical delay vibrating means vibrates the length of the optical path for the corresponding one of the excitation light and the probe light, the frequency analyzing means performing the frequency analysis based on the thus changed or set vibration frequency.

6. A terahertz wave spectrometer as claimed in claim 1, wherein at least one of the terahertz wave generator and the terahertz wave detector is constructed from an optical switching device.

7. A terahertz wave spectrometer as claimed in claim 1, wherein at least one of the terahertz wave generator and the terahertz wave detector is constructed from an electro-optic crystal.

8. A terahertz wave spectrometer as claimed in claim 1, further comprising sample moving means moving the sample two-dimensionally, thereby causing the spectroscopic processing means to perform two-dimensional spectroscopic measurement on the sample.

9. A terahertz wave spectrometer as claimed in claim 1, wherein the terahertz wave detector is constructed from a two-dimensional detector, in which a plurality of terahertz wave detecting portions are arranged two-dimensionally, the spectroscopic processing means including a plurality of frequency analyzing means, the plural terahertz wave detecting portions being connected to the plural frequency analyzing means, respectively, each frequency analyzing means performing frequency analysis on a detection signal obtained by the corresponding terahertz wave detecting portion, thereby attaining two-dimensional spectroscopic measurement on the sample.

10. A terahertz wave spectrometer as claimed in claim 1, wherein the excitation light optical system includes an optical chopper controlling on and off of the excitation light.

11. A terahertz wave spectrometer as claimed in claim 1, wherein the spectroscopic processing means further includes analyzing means determining frequency analysis of the terahertz wave, which is affected by the sample and which indicates the spectroscopic information of the sample, based on the frequency-analysis result of the detection signal obtained by the frequency analyzing means.

12. A terahertz wave spectrometer as claimed in claim 1, wherein the frequency analyzing means detects a desired frequency component of the detection signal by performing the frequency-domain measurement.

13. A terahertz wave spectrometer as claimed in claim 12, wherein the frequency analyzing means is constructed from a spectrum analyzer.

14. A terahertz wave spectrometer as claimed in claim 13, wherein the spectrum analyzer is set to a zero span mode.

15. A terahertz wave spectrometer as claimed in claim 12, wherein the frequency analyzing means includes a band pass filter selecting the desired frequency component, wherein the spectroscopic processing means further includes frequency setting/changing means controlling the optical delay vibrating means and changing or setting the value of the vibrating frequency, at which the optical delay vibrating means vibrates the length of the optical path of the corresponding one of the excitation light and the probe light, to a value that corresponds to a frequency value of the desired frequency component to be selected by the band pass filter.

16. A terahertz wave spectrometer as claimed in claim 12, wherein the terahertz wave detector is constructed from a two-dimensional detector, in which a plurality of terahertz wave detecting portions are arranged two-dimensionally, the spectroscopic processing means including a plurality of band pass filters, the plural terahertz wave detecting portions being connected to the plural band pass filters, respectively, each band pass filter performing frequency-domain measurement on a detection signal obtained by the corresponding terahertz wave detecting portion to select the desired frequency component, thereby attaining two-dimensional spectroscopic measurement on the sample.

17. A terahertz wave spectrometer as claimed in claim 12, wherein the excitation light optical system includes an optical chopper controlling on and off of the excitation light at a predetermined driving frequency, the frequency analyzing means detecting, by performing frequency-domain measurement, a frequency component of the detection signal that is determined with respect to the predetermined driving frequency.

18. A terahertz wave spectrometer as claimed in claim 17, wherein the frequency analyzing means includes a spectrum analyzer.

19. A terahertz wave spectrometer as claimed in claim 16, wherein the frequency analyzing means includes a band pass filter.

* * * * *